US011932147B2

(12) United States Patent
Kaku et al.

(10) Patent No.: US 11,932,147 B2
(45) Date of Patent: Mar. 19, 2024

(54) SEAT

(71) Applicant: TS TECH CO., LTD., Asaka (JP)

(72) Inventors: Hiroyuki Kaku, Tochigi (JP); Atsushi Kusano, Tochigi (JP); Hiroyuki Numajiri, Tochigi (JP); Satoshi Fujita, Tochigi (JP); Takako Miyoshi, Tochigi (JP); Munetaka Kowa, Tochigi (JP); Ryuichiro Hirose, Tochigi (JP); Yoshikazu Ito, Tochigi (JP); Yosuke Higashi, Tochigi (JP); Satoshi Suzuki, Tochigi (JP); Ryosuke Sato, Tochigi (JP); Kento Uetake, Tochigi (JP); Yasuharu Otsuka, Tochigi (JP); Satoru Kaneda, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 77 days.

(21) Appl. No.: 16/978,601

(22) PCT Filed: Feb. 28, 2019

(86) PCT No.: PCT/JP2019/007763
§ 371 (c)(1),
(2) Date: Sep. 4, 2020

(87) PCT Pub. No.: WO2019/172063
PCT Pub. Date: Sep. 12, 2019

(65) Prior Publication Data
US 2021/0039537 A1    Feb. 11, 2021

(30) Foreign Application Priority Data

Mar. 5, 2018    (JP) .................................. 2018-038554
Mar. 5, 2018    (JP) .................................. 2018-038555
Mar. 5, 2018    (JP) .................................. 2018-038559

(51) Int. Cl.
*B60N 2/90*    (2018.01)
*A47C 7/62*    (2006.01)
(Continued)

(52) U.S. Cl.
CPC .................. *B60N 2/90* (2018.02); *A47C 7/62* (2013.01); *B60N 2/002* (2013.01); *B60R 21/01516* (2014.10); *B60R 21/01542* (2014.10)

(58) Field of Classification Search
CPC .. B60N 2/90; B60N 2/002; A47C 7/62; B60R 21/01516; B60R 21/01542
See application file for complete search history.

(56) References Cited

U.S. PATENT DOCUMENTS 6,392,550 B1    5/2002    Najor
8,478,486 B2    7/2013    Kato et al.
(Continued)

FOREIGN PATENT DOCUMENTS

CN    102271982    12/2011
DE    202007011704 U1    12/2007
(Continued)

OTHER PUBLICATIONS

International Search Report and Written Opinion issued for International Patent Application No. PCT/JP2019/007763, dated May 28, 2019, 19 pages including English translation.
(Continued)

*Primary Examiner* — Anthony D Barfield
(74) *Attorney, Agent, or Firm* — Hamre, Schumann, Mueller & Larson, P.C.

(57) ABSTRACT

Disclosed is a seat including: sensors which includes a first cushion sensor provided at a seat cushion in a position corresponding to buttocks of an occupant, a second cushion sensor provided at the seat cushion and located farther frontward than the first cushion sensor, a first back sensor
(Continued)

provided at a seat back and located in a lower position thereof, and a second back sensor provided at the seat back and located above the first back sensor; and a controller connected to the sensors and thereby allowed to acquire pressure values from the respective sensors. The controller is configured to identify the motion of the occupant based on outputs of at least two sensors of the first cushion sensor, the second cushion sensor, the first back sensor, and the second back sensor.

22 Claims, 27 Drawing Sheets

(51) Int. Cl.
  *B60N 2/00* (2006.01)
  *B60R 21/015* (2006.01)

(56) References Cited

U.S. PATENT DOCUMENTS

| | | | |
|---|---|---|---|
| 9,703,380 | B2 | 7/2017 | Koyama |
| 9,795,322 | B1 | 10/2017 | Karunaratne et al. |
| 10,046,671 | B2 * | 8/2018 | Seiller .................... B60N 2/002 |
| 10,967,758 | B2 | 4/2021 | Mizoi |
| 2011/0178680 | A1 | 7/2011 | Kato et al. |
| 2011/0269601 | A1 | 11/2011 | Nelson et al. |
| 2015/0366350 | A1 | 12/2015 | Di Censo et al. |
| 2015/0370329 | A1 | 12/2015 | Koyama |
| 2017/0169690 | A1 | 6/2017 | Pfeiffer et al. |
| 2017/0251979 | A1 | 9/2017 | Franz et al. |
| 2018/0052982 | A1 | 2/2018 | Kingsbury et al. |
| 2018/0304774 | A1 | 10/2018 | Mizoi |
| 2021/0016187 | A1 * | 1/2021 | Lee ........................ B60N 2/002 |

FOREIGN PATENT DOCUMENTS

| | | |
|---|---|---|
| EP | 3251889 | 12/2017 |
| JP | H0477355 U | 7/1992 |
| JP | H04309996 A | 11/1992 |
| JP | H1164131 | 3/1999 |
| JP | 2001141580 | 5/2001 |
| JP | 2004249833 | 9/2004 |
| JP | 2012157580 | 8/2012 |
| JP | 2016004541 | 1/2016 |
| JP | 2017065504 | 4/2017 |
| JP | 2017081194 | 5/2017 |
| WO | 2017069235 | 4/2017 |

OTHER PUBLICATIONS

Office Action issued for Japanese Patent Application No. 2018-038559, Dispatch Date: Mar. 2, 2021, 5 pages including English translation.

Office Action issued for Japanese Patent Application No. 2018-038555, Dispatch Date: Apr. 13, 2021, 7 pages including English translation.

Office Action issued for Japanese Patent Application No. 2018-038559, Dispatch Date: May 11, 2021, 7 pages including English translation.

Extended European Search Report issued for European Patent Application No. 19763640.0, dated Apr. 1, 2021, 8 pages.

First Examination Report issued for Indian Patent Application No. 202047041145, Dispatch Date: Mar. 22, 2021, 6 pages.

First Office Action issued for Chinese Patent Application No. 201980017484.1, dated Feb. 25, 2022, 21 pages including English translation.

Office Action issued for Japanese Patent Application No. 2021-080720, dated May 17, 2022, 6 pages including English translation.

Office Action issued in Japanese Patent Application No. 2021-164386, dated Dec. 13, 2022, with English translation (7 pages).

Office Action issued in Chinese Patent Application No. 201980017484.1, dated Nov. 28, 2022, with English translation (24 pages).

Notification of Reason(s) for Refusal issued for Japanese Patent Application No. 2021-153724, dated Jan. 10, 2023, 7 pages including English translation.

Third Office Action issued for Chinese Patent Application No. 201980017484.1, dated May 31, 2023, 27 pages including English translation.

Communication pursuant to Article 94(3) EPC, issued for European Patent Application No. 19763640.0, dated Sep. 22, 2023, 5 pages.

* cited by examiner

FIG.3
(a)
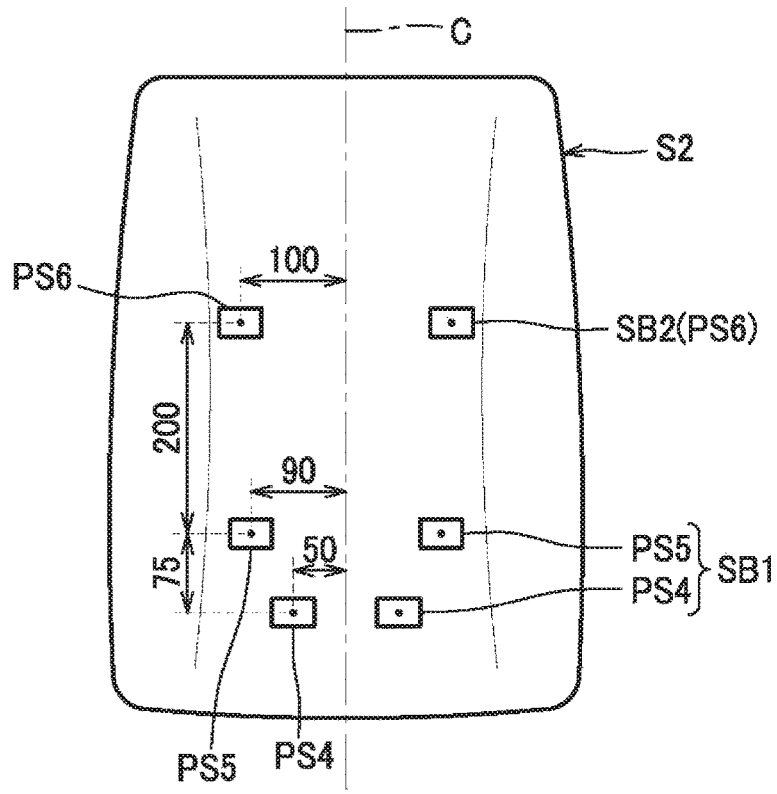
(b)
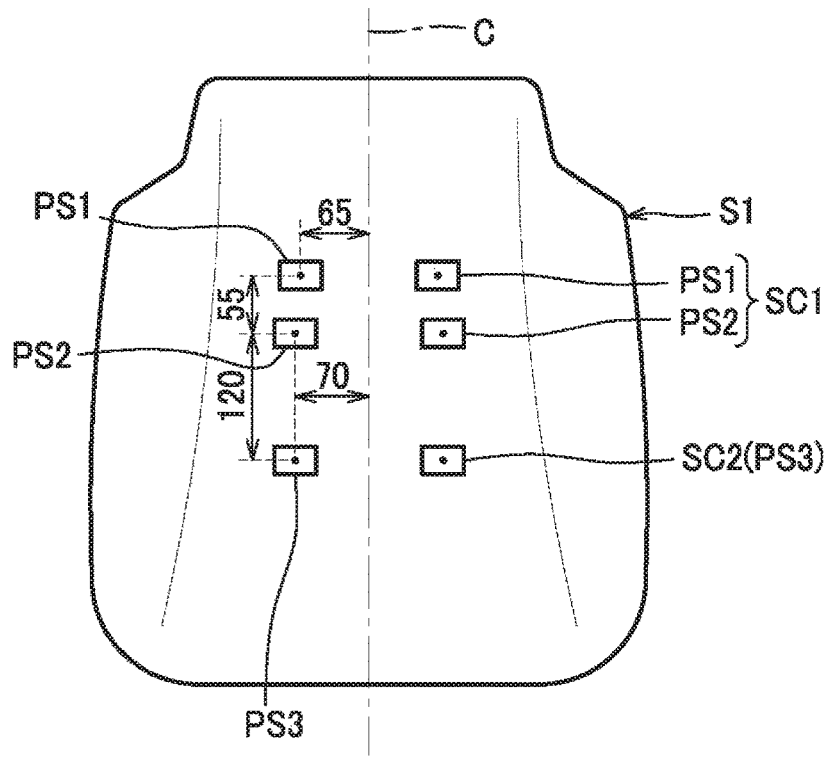

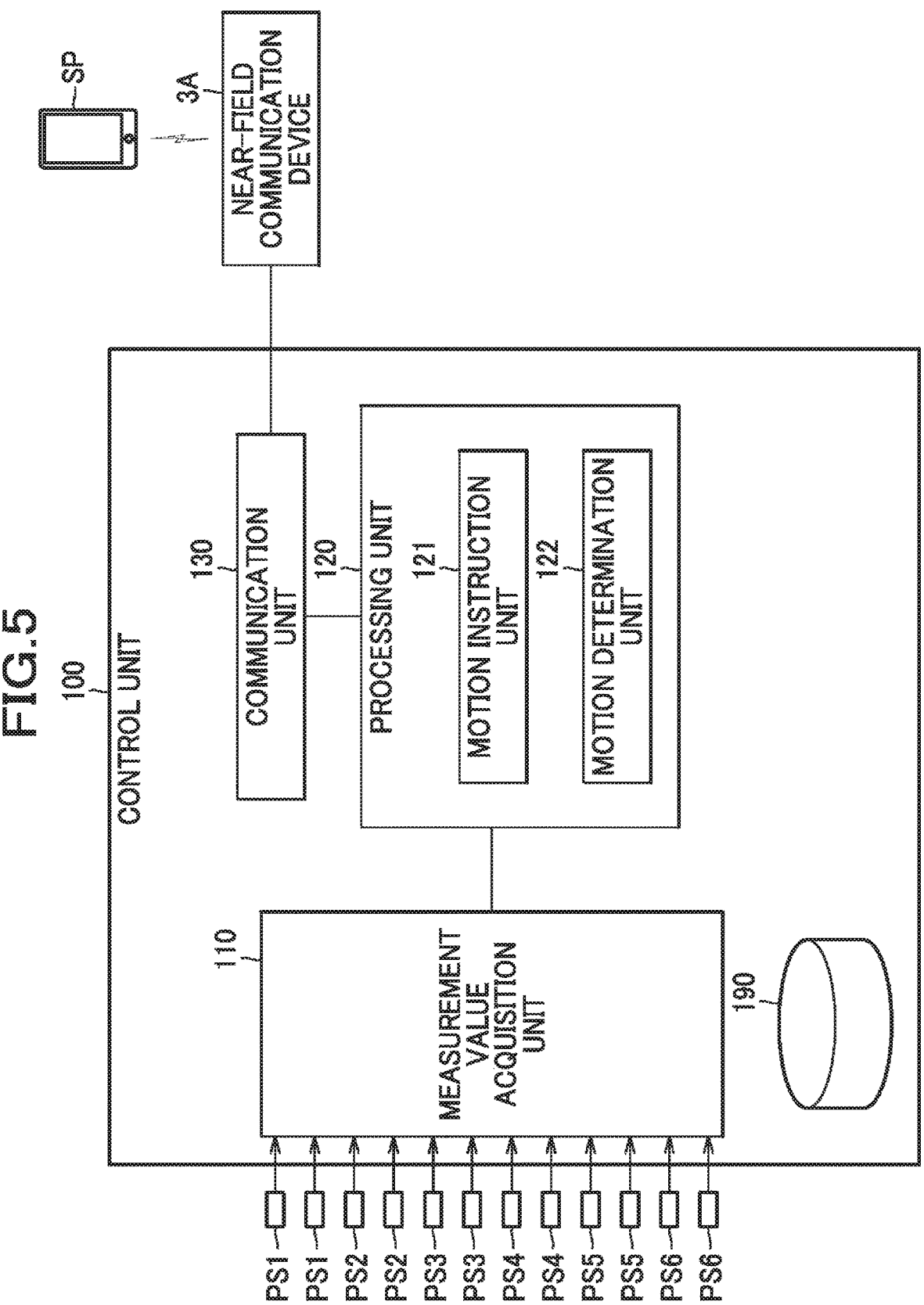

FIG.6

| MOTION CODE MC | MOTION | SENSOR OUTPUTTING PRESSURE VALUE GREATER THAN WHEN REFERENCE POSTURE IS ASSUMED | SENSOR OUTPUTTING PRESSURE VALUE SMALLER THAN WHEN REFERENCE POSTURE IS ASSUMED |
|---|---|---|---|
| 1R 1L | HEEL LIFT (CALF EXERCISE) | SC1(PS2) (LIFTED FOOT SIDE) | SC2(PS3) (SAME SIDE) |
| 2R 2L | FOOT LIFT | SC1(PS2) SB1(PS4) (LIFTED FOOT SIDE) | SC2 (PS3, SAME SIDE) SB2 (PS6, OPPOSITE SIDE) |
| 3 | SIT UP STRAIGHT | SC1(PS1) | SB1(PS5) SB2(PS6) |
| 4 | SCAPULAE PRESS | SC1(PS1) SB2(PS6) | SB1(PS4) |
| 5R 5L | UPPER BODY TURN | SC1(PS1) SB1(PS4) (FACING SIDE) | SB1(PS4) SB2(PS6) (OPPOSITE SIDE) |

FIG.7

WHOLE-BODY COURSE

| No. | MOTION CODE MC | DURATION [ms] |
|---|---|---|
| 1 | 1R | 1000 |
| 2 | 1L | 1000 |
| 3 | 1R | 1000 |
| ⋮ | ⋮ | ⋮ |
| 100 | 2R | 500 |
| 101 | 2L | 500 |
| ⋮ | ⋮ | ⋮ |
| 200 | 5R | 1000 |
| 201 | 5L | 1000 |
| ⋮ | ⋮ | ⋮ |
| 300 | 4 | 3000 |
| 301 | 0 | 3000 |
| ⋮ | ⋮ | ⋮ |
| 400 | 3 | 4000 |
| 401 | 0 | 4000 |
| 402 | 3 | 4000 |
| ⋮ | ⋮ | ⋮ |
| 499 | EOL | — |

FIG.8

| MC | MESSAGE |
|---|---|
| 1R | Feet not moving. Use your calves to lift heels up. |
| 1L | Feet not moving. ... |
| 2R | ...... |
| 2L | ...... |
| ⋮ | ...... |
| 5R | ...... |
| 5L | Turn your shoulders to twist upper body. |

FIG.9

| MC | MESSAGE |
|---|---|
| 1R | Heel lift looks not high enough. Lift your heels higher. |
| 1L | Heel lift looks not high enough. Lift your heels higher. |
| ⋮ | ...... |
| 5L | Turn your shoulders large. |

FIG.10

| MC | MCJ | MESSAGE |
|---|---|---|
| 1R | 2R | Keep your feet on floor, use your calves to lift heels up. |
| ⋮ | ⋮ | ⋮ |
| 2R | 1R | Lift your feet up apart from the floor. |
| ⋮ | ⋮ | ⋮ |

| CONDITIONS | IMITATIVE WORDS |
|---|---|
| $1.5 \leq TS/TS_n$ | fura-fura (tottering) |
| $1.2 \leq TS/TS_n < 1.5$ | nosshi-nosshi (lumping along) |
| $0.7 \leq TS/TS_n < 1.2$ | suta-suta (walking at brisk pace) |
| $TS/TS_n < 0.7$ | dota-dota (walking with heavy steps noisily) |

FIG.23

| NUMBER OF STEPS | EXERCISE LEVELS |
|---|---|
| ~60 | slow rambling |
| 61~110 | usual daily-life walking |
| 111~140 | exercise walking |
| 141~240 | jogging |
| 240~ | dashing |

SEAT

TECHNICAL FIELD

The present invention relates to a seat capable of identifying motion of an occupant seated thereon.

BACKGROUND ART

An apparatus having a pressure sensor or the like provided in a driver's seat to evaluate a posture of a seated person is hitherto known in the art (Patent document 1). Another apparatus which uses a pressure sensor or the like provided in a seat to evaluate a fatigued state of a seated person and causes the seat to make a motion based on the results of evaluation is known in the art (Patent document 2).

CITATION LIST

Patent Literature

Patent document 1: JP H11-064131 A
Patent document 2: JP 2017-065504 A

SUMMARY OF INVENTION

However, the apparatus of Patent document 1 merely presenting the results of evaluation made on the posture of the seated driver disadvantageously does not appear to be utilized in its full potential; thus, new added values have been sought for. On the other hand, the apparatus of Patent document 2 producing a motion of the seat to bring about recovery from fatigue would merely impart such a passive physical exercise as could not be expected to bring about sufficient recovery from fatigue. Rather, the inventors named and colleagues not named in this application have contrived that if an occupant is encouraged to perform an active physical exercise, this can not only relieve fatigue effectively but also realize more pleasant journey. While there is some risk of occurrence of traveler's thrombosis resulting from long flights on an airplane, or long journeys on a long-distance bus or other vehicles, such traveler's thrombosis could possibly be restrained by physical exercises taken pleasantly in the vehicle.

Further, getting exercises while seated, even on a seat other than those for vehicles, would possibly be a good practice for achieving healthy life.

Unfortunately, the known seats are incapable of identifying motion of an occupant seated thereon, and no way would realize such an enjoyable on-seat experience.

Against this backdrop, it would be desirable to provide a seat capable of identifying motion of a person seated thereon.

Disclosed herein is one aspect of a seat which comprises a seat body, sensors configured to acquire measurement values for use in identifying motion of an occupant seated on the seat body, and a controller connected to the sensors and thereby allowed to acquire the measurement values from the sensors. The seat body comprises a seat cushion and a seat back, and the sensors comprise a first cushion sensor provided at the seat cushion in a position thereof corresponding to buttocks of the occupant, a second cushion sensor provided at the seat cushion and located farther frontward than the first cushion sensor, a first back sensor provided at the seat back and located in a lower position thereof, and a second back sensor provided at the seat back and located above the first back sensor.

The controller is configured to identify the motion of the occupant based on outputs of at least two sensors of the first cushion sensor, the second cushion sensor, the first back sensor, and the second back sensor. Adopted as the sensors, for example, may be ones which are capable of acquiring, as the measurement values, values of pressure from the occupant seated on the seat body.

With this configuration, the motion of the occupant can be identified by a combination of measurement values (pressure values) acquired from at least two sensors chosen among at least four sensors of the first cushion sensor and the second cushion sensor located apart one behind the other at the seat cushion, and the first back sensor and the second back sensor located apart one above the other at the seat back.

To be more specific, in cases where pressure values are adopted as the measurement values, the controller may be configured to make evaluations of pressure values with respect to those acquired when a reference posture is assumed, and if a pressure value of the first cushion sensor goes up and a pressure value of the second cushion sensor goes down, then determine that a heel lift motion has been done.

The controller may be configured to make evaluations of pressure values with respect to those acquired when a reference posture is assumed, and if pressure values of the first cushion sensor and the first back sensor go up and a pressure value of the second cushion sensor goes down, then determine that a foot lift motion has been done.

The controller may be configured to make evaluations of pressure values with respect to those acquired when a reference posture is assumed, and if a pressure value of the first cushion sensor goes up and a pressure value of the first back sensor goes down, then determine that a sit-up-straight motion has been done.

The controller may be configured to make evaluations of pressure values with respect to those acquired when a reference posture is assumed, and if pressure values of the first cushion sensor and the second back sensor go up and a pressure value of the first back sensor goes down, then determine that a scapulae press-against-seat-back motion has been done.

The first back sensor may comprise at least one right first back sensor and at least one left first back sensor, the first cushion sensor may comprise at least one right first cushion sensor and at least one left first cushion sensor, and the second back sensor may comprise at least one right second back sensor and at least one left second back sensor. Herein, the controller may be configured to make evaluations of pressure values with respect to those acquired when a reference posture is assumed, and if pressure values of the right first cushion sensor and the right first back sensor go up and pressure values of the left first back sensor and the left second back sensor go down, then determine that an upper-body turn-right motion has been done, while if pressure values of the left first cushion sensor and the left first back sensor go up and pressure values of the right first back sensor and the right second back sensor go down, then determine that an upper-body turn-left motion has been done.

The second back sensor may preferably be located above a position distanced 300 mm upward from a seat surface of the seat cushion as measured along a seat surface of the seat back. With this configuration, the pressure from the shoulder of the occupant can be detected by the second back sensor.

The second cushion sensor may preferably be located frontward of a position distanced 280 mm frontward from a seat surface of the seat back as measured along a seat surface of the seat cushion. With this configuration, the upward/downward motion of the thighs can be detected properly.

According to the above-described embodiments of the seat, the motion of the occupant can be identified by the combination of the pressure values acquired from at least two sensors.

Furthermore, from another aspect, a seat comprising a seat body, sensors configured to acquire measurement values for use in identifying motion of an occupant seated on the seat body, and a controller connected to the sensors and thereby allowed to acquire the measurement values from the sensors is disclosed. Herein the controller comprises: a motion instruction unit configured to give the occupant an instruction to do a predetermined motion; and a motion determination unit configured to identify the motion of the occupant based on the measurement values acquired from the sensors, wherein the motion determination unit is configured to make a determination, after the motion instruction unit gives the instruction, as to whether or not the occupant is doing the predetermined motion.

With this configuration, the controller of the seat is configured such that the occupant is given an instruction to do a motion by the motion instruction unit, and a determination is made by the motion determination unit as to whether or not the occupant, after instructed to do the predetermined motion by the motion instruction unit, is doing the predetermined motion. Accordingly, the occupant can be encouraged to actively do a motion, and the seat can respond thereto in relation to the quality of the motion done, so that a seat having an interactive relationship with the occupant can be provided.

It is to be understood that the sensors may preferably be configured to acquire, as the measurement values, values of pressure from an occupant seated on the seat body. This is because such acquisition of the values of pressure from an occupant would enable precise identification of the motion of the occupant.

In the seat described above, the motion instruction unit may be configured to give the occupant an instruction to do a predetermined motion by at least one of sound, light, image, moving image, textual characters, vibrations, and warmth or coldness sensation.

The seat described above may preferably be configured such that if the motion determination unit determines that the occupant is not doing the predetermined motion, the motion instruction unit then gives the instruction again to do the predetermined motion. With this configuration, the occupant can be encouraged to do a motion actively.

The seat described above may preferably be configured such that if the motion determination unit determines that the predetermined motion the occupant is doing is deficient in scale, the motion instruction unit then gives the occupant an instruction to do the predetermined motion on a larger scale. With this configuration, the occupant can be encouraged to do a larger motion, afforded increased pleasure on the seat, and gifted with a healthy life.

The seat described above may preferably be configured such that if the motion determination unit determines that a motion the occupant is doing is different from the motion instructed by the motion instruction unit, the motion instruction unit then notifies the occupant of a proper way to do the motion. With this configuration, the occupant can be encouraged to do a health-promoting exercise. Moreover, the occupant, when intends to manipulate something by doing a specific motion, can be instructed to perform accurate manipulation.

According to the embodiments of the seat with the controller comprising the motion determination unit and the motion instruction unit as described above, a seat having interactive relationship with the occupant can be provided. Furthermore, the occupant can be encouraged to do a motion actively, thus afforded increased pleasure on the seat, gifted with a healthy life, and otherwise provided with benefits.

Furthermore, from another aspect, a seat comprising a seat body installed in a vehicle, sensors configured to acquire measurement values for use in identifying motion of an occupant seated on the seat body, and a controller connected to the sensors and thereby allowed to acquire the measurement values from the sensors is disclosed. Herein, the controller is connected to and thus allowed to communicate with an on-board device to be operated, located in the vehicle, and configured to output, based on the measurement values, a signal for operating the on-board device.

With this configuration, in which the controller outputs the measurement values acquired from the sensors as a signal for operating the on-board device, the occupant seated on the seat can operate the on-board device by doing a motion, for example moving his/her upper body or legs, and so forth, on the seat body.

Therefore, the operation of the on-board device which would conventionally require manual operations of the on-board device or the controller of the on-board device can be carried out through body motions on the seat. For example, even in cases a person unwilling to use his/her hand or a person with a hand disability is to operate, he/she can operate the on-board device by moving a part of his/her body or tensing his/her muscle or otherwise.

The sensors may preferably be so located as to be allowed to detect a state of a seat surface that faces an occupant seated on the seat body.

This configuration enables the occupant to operate the on-board device by changing the state of the seat surface, and thus makes the operation easier.

The on-board device may include a display, and the controller may be configured to be capable of outputting a signal for manipulating a cursor or an icon shown on the display.

With this configuration, if the on-board device is embodied as a personal computer, a navigation system or a smartphone and configured to include a display, operation of them is made possible.

It is to be understood that the cursor is a mark for pointing to positions or icons on the display, and typically includes, in situations where a personal computer is used, a pointer operated with a mouse, an indication of selection (indicated by inverse video characters or differentiated colors in many cases) operated with a mouse or a keyboard, and so forth. It is also to be understood that the icon is an image shown and to be operated on the display, and includes a folder, a file and a button in the case of a personal computer operating system, a character in the case of a game application, a button in the case of a navigation system, and so forth.

It is preferable that the controller be configured to output the signal based on the measurement values, provided that the measurement values exceed predetermined threshold values.

With this configuration, an inadvertent operation of the on-board device can be restrained.

The controller may have operation modes which comprise a first operation mode in which the signal is outputted based on the measurement values, and a second operation mode in which the signal is not outputted, and may be configured to operate in the first operation mode only after providing notification to prompt the occupant to do a motion via the on-board device or other devices.

In the seat described above, the sensors may be configured to be capable of acquiring values of pressure from an occupant seated on the seat body.

The sensors may be pressure sensors, and the pressure sensors may comprise a first pressure sensor and a second pressure sensor located in a position different from a position of the first pressure sensor. Herein, the controller may be configured such that to an operation of the on-board device as determined based on a measurement value acquired from the first pressure sensor is assigned a first operation, and to an operation of the on-board device as determined based on a measurement value acquired from the second pressure sensor is assigned a second operation.

With this configuration, the first operation and the second operation can be executed respectively based on the measurement values acquired by different sensors, i.e., the first sensor and the second sensor, so that an operating error can be restrained.

The controller may be configured to output the signal based on change of the measurement values acquired from the sensors.

The seat described above may be configured such that a plurality of seat bodies are provided in the vehicle, and the sensors are provided in each of the seat bodies, wherein the controller is configured to acquire the measurement values from each of the seat bodies, and to output the signal based on the measurement values.

According to the embodiments of the seat in which the controller is configured to output, based on the measurement values acquired from the sensors, the signal for operating the on-board device in a vehicle, the occupant seated on the seat can operate the on-board device by means of the seat.

Since the operation of the on-board device can be performed by the occupant changing the state of the seat surface, the operation is easy to perform.

Since the signal is outputted based on the measurement values on condition that the measurement values exceed predetermined threshold values, an inadvertent operation of the on-board device can be restrained.

Since to the operation of the on-board device as determined based on the measurement value acquired from the first pressure sensor is assigned a first operation, and to the operation of the on-board device as determined based on the measurement value acquired from the second pressure sensor is assigned a second operation, an operating error can be restrained.

BRIEF DESCRIPTION OF DRAWINGS

FIG. 3 includes diagrams for explaining arrangement of sensors, of which (a) is a front view of a seat back and (b) is a top view of a seat cushion.

FIG. 5 is a block diagram for explaining a vehicle seat and system configuration according to a first embodiment.

FIG. 6 is a table for explaining criteria for determination of motions.

FIG. 7 is an example of motion list for a whole-body course.

FIG. 8 is a message table to be used when it is determined that no motion is being done.

FIG. 9 is a message table to be used when it is determined that the motion is deficient.

FIG. 10 is a message table to be used when it is determined that the motion being done is different from the motion instructed.

FIG. 23 is a table for determination of exercise levels.

DESCRIPTION OF EMBODIMENTS

First Embodiment

Hereinafter, a detailed description will be given of a first embodiment with reference made to accompanying drawings where appropriate.

Figure 1:
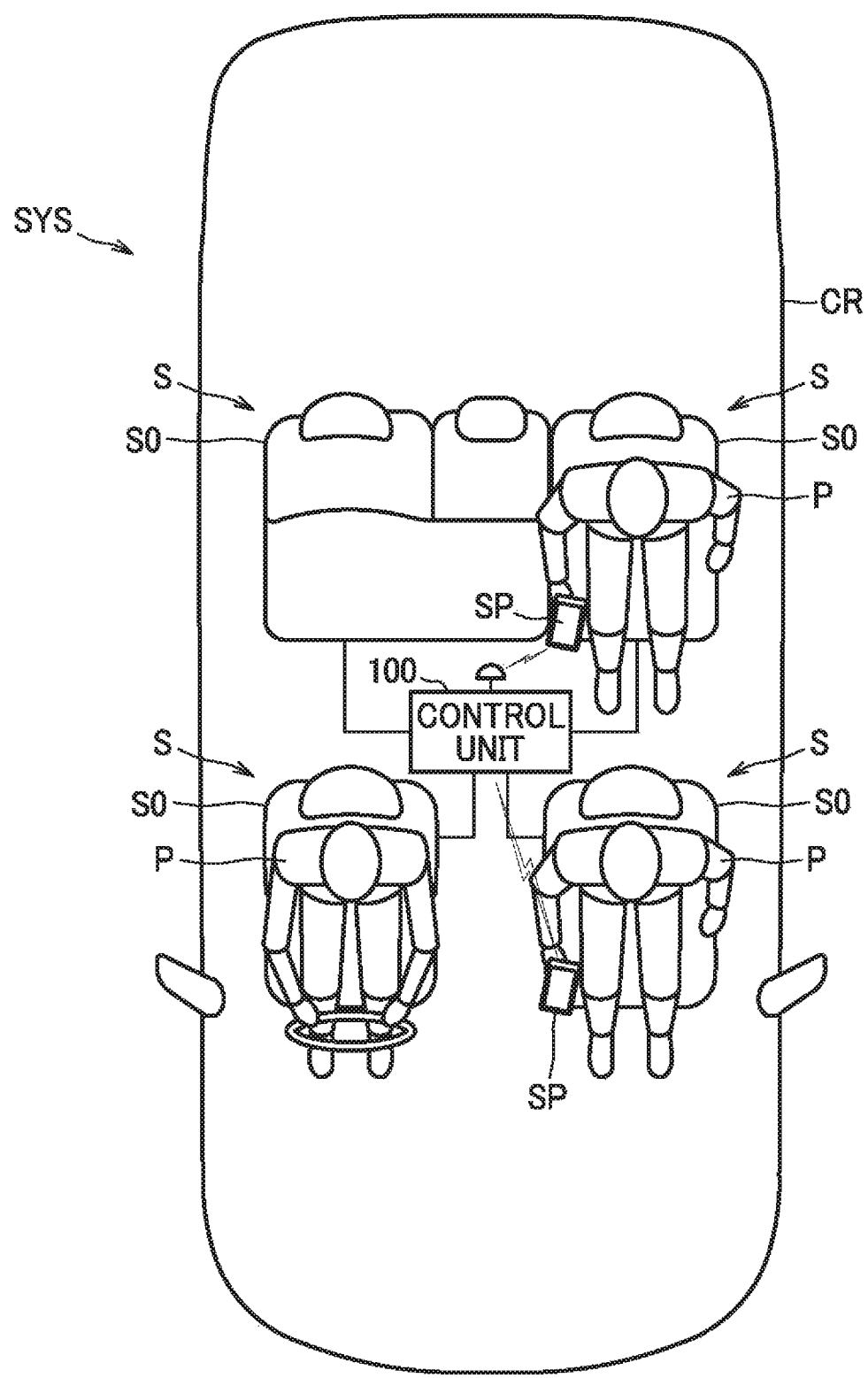
FIG. 1 is a diagram for explaining a general configuration of a system using vehicle seats.

As shown in FIG. 1, a vehicle seat S as an example of a seat is configured as a car seat to be installed in a car CR by way of example. The vehicle seat S comprises a seat body S0 and a control unit 100 as an example of a controller. The car CR is provided with two front seats and two rear seats; each of these four seats is configured as a vehicle seat S. Provided in the car CR is a control unit 100 which integrates information gathered from among the four vehicle seats S, causes them to operate in concert with one another, and communicates with a smartphone SP as an example of a terminal (i.e., on-board device) to be used by each occupant P in the car CR.

To sum up, the car CR comprises the control unit 100 and a plurality of seat bodies S0 which constitute a system SYS for the vehicle seats S.

Figure 2:
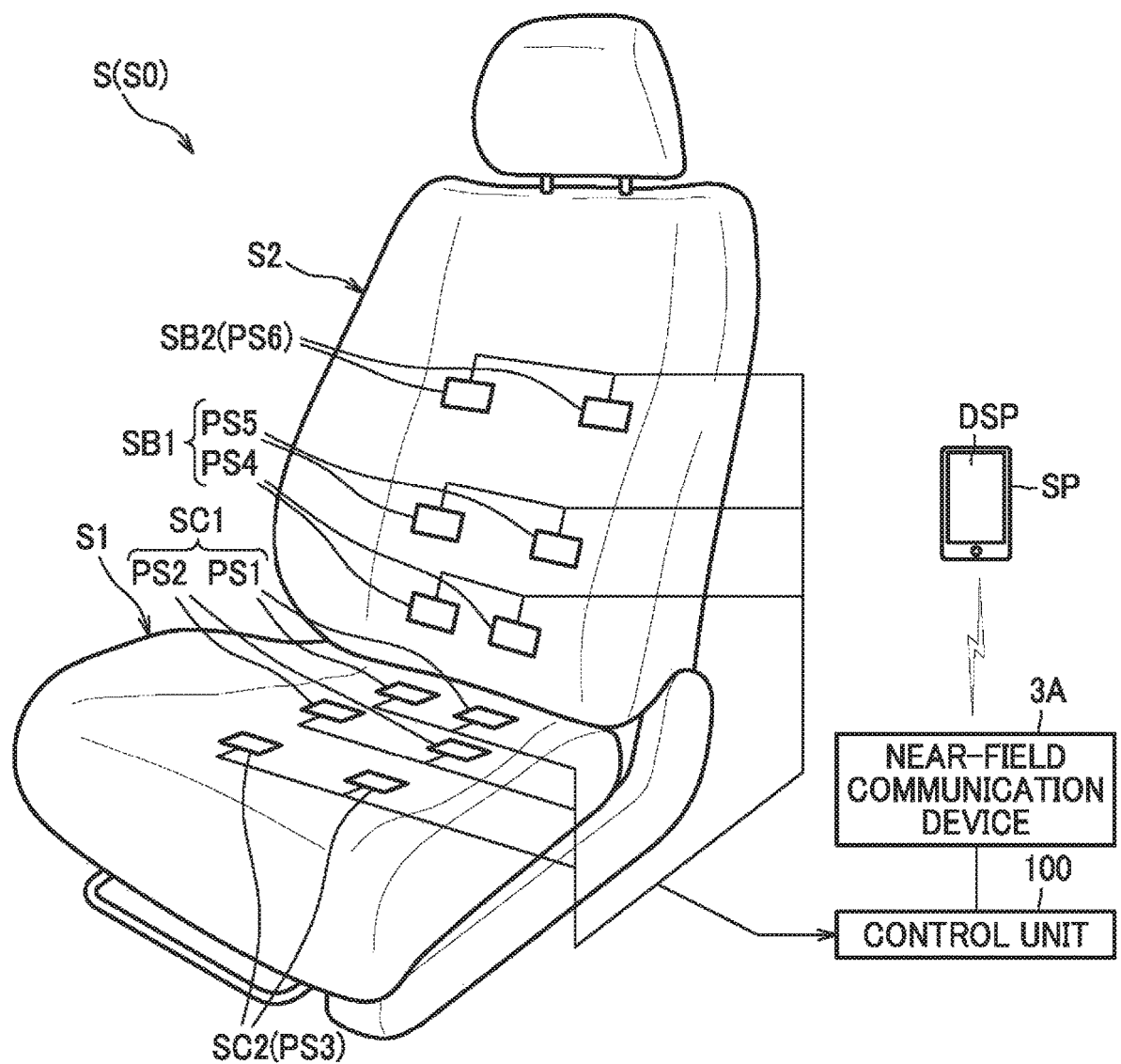
FIG. 2 is a diagram for explaining a configuration of each vehicle seat.

As shown in FIG. 2, a seat body S0 includes a seat cushion S1 and a seat back S2. A plurality of pressure sensors PS1 to PS6 are provided under outer coverings of the seat cushion S1 and the seat back S2. The pressure sensors PS1 to PS6 are sensors configured to acquire measurement values for use in identifying motion of an occupant P seated on the seat body S0. The pressure sensors PS1 to PS6 are so located as to be allowed to detect a state of a seat surface that faces an occupant P seated on the seat body S0, to acquire values of pressure from the occupant P seated on the seat body S0. The control unit 100 is connected to the pressure sensors PS1 to PS6 and thus allowed to acquire pressure values from each of the pressure sensors PS1 to PS6.

The respective pressure sensors PS1 to PS6 are provided in pairs, each located left and right, symmetric with respect to a laterally central position of the vehicle seat S.

To be more specific, as also seen in FIG. 3 (b), the seat cushion S1 has the pressure sensors PS1 to PS3 provided thereat.

The pressure sensors PS1 are provided in positions corresponding to the lowermost portions of ischial bones of an occupant P. The load of the occupant P is borne largest at these positions. The pressure sensors PS1 may be located, for example, in positions 60 to 70 mm, e.g., 65 mm, apart from the laterally central position C of the vehicle seat S to the left and to the right.

The pressure sensors PS2 are located a little frontward of the pressure sensors PS1, and may be located, for example, in positions 50 to 60 mm, e.g., 55 mm, apart from the pressure sensors PS1 frontward, and 65 to 75 mm, e.g., 70 mm, apart from the central position C to the left and to the right. The pressure sensors PS1 and the pressure sensors PS2 are an example of a first cushion sensor provided at the seat cushion S1 in a position thereof corresponding to buttocks of the occupant P. The first cushion sensor comprises at least one right cushion sensor (pressure sensors PS1, PS2) and at least one left cushion sensor (pressure sensors PS1, PS2).

The pressure sensors PS1 and the pressure sensors PS2 are both intended for measurements of pressure from the buttocks of an occupant P, and only providing either of the pressure sensors PS1 or PS2 may also be appropriate. Therefore, in the description that follows, the pressure sensors PS1 and the pressure sensors PS2 are also referred to collectively as a first cushion sensor SC1 for convenience' sake.

The pressure sensors PS3 are located frontward of and distanced far from the pressure sensors PS1 and the pressure sensors PS2. The pressure sensors PS3 are an example of a second cushion sensor provided at the seat cushion S1 and located farther frontward than the first cushion sensor SC1. In the description that follows, the pressure sensors PS3 are also referred to as a second cushion sensor SC2.

The pressure sensors PS3 are located under the thighs of the occupant P, and allowed to measure values of pressure from the thighs of the occupant P. The pressure sensors PS3 may be located in positions 110 to 130 mm, e.g., 120 mm, apart from the pressure sensors PS2 (i.e., frontward, 175 mm apart from the pressure sensors PS1), and 65 to 75 mm, e.g., 70 mm, apart from the central position C to the left and to the right.

Figure 4:
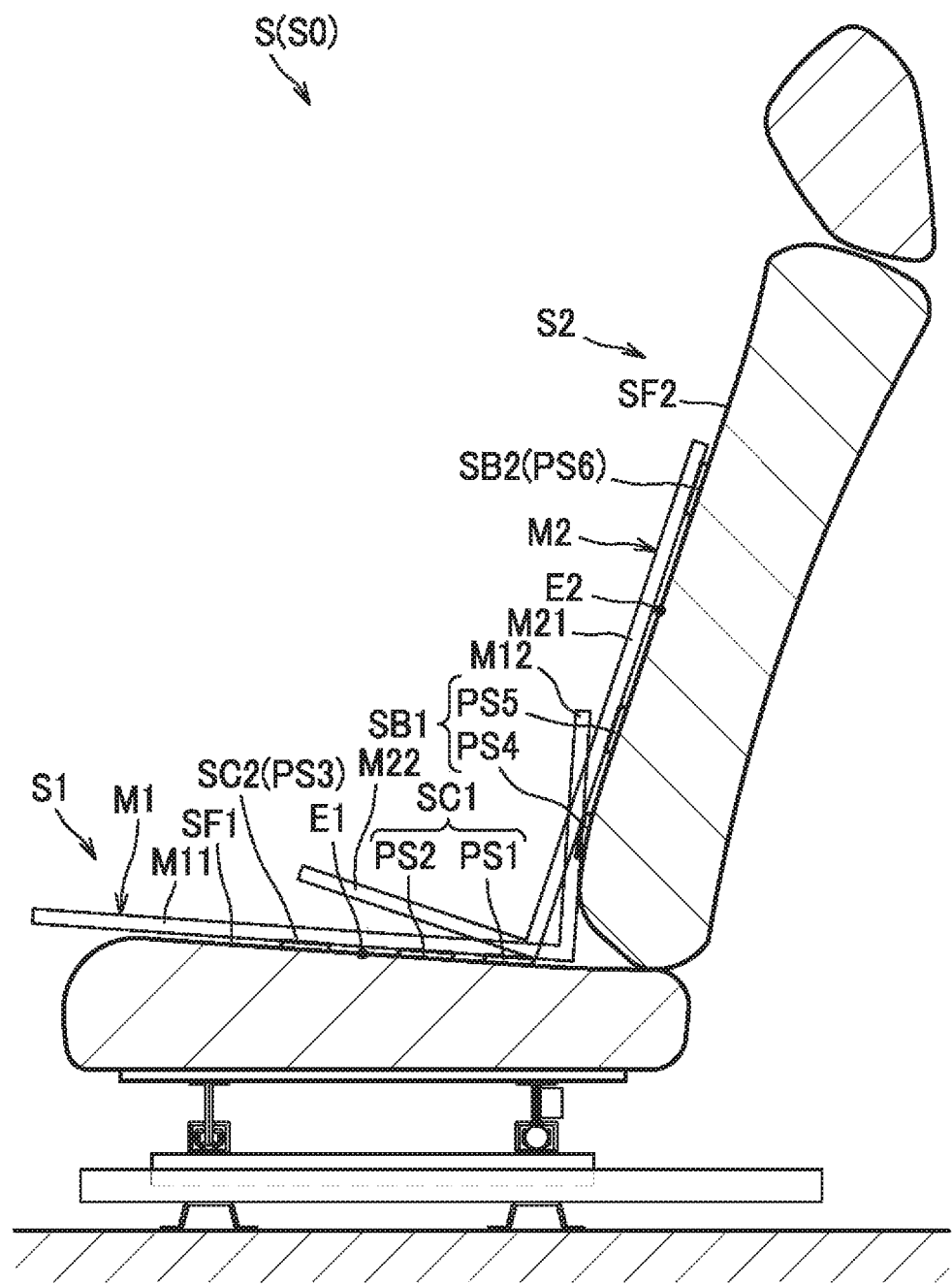
FIG. 4 is a sectional view of a seat for explaining arrangement of sensors.

As shown in FIG. 4, the second cushion sensor SC2 may preferably be located frontward of a position E1 distanced 280 mm frontward from a seat surface SF2 of the seat back S2 as measured along a seat surface SF1 of the seat cushion S1. It is to be understood that the first cushion sensor SC1 is located rearward of the position E1. The position E1 as mentioned herein is measured by placing one arm M11 of an L-shaped framing square M1 on the seat surface SF1 of the seat cushion S1, bringing the other arm M12 into contact with the seat surface SF2 of the seat back S2, and reading the scale of the arm M11. In embodiments where the seat back S2 has an adjustable shape (e.g., with lumbar supports), it will suffice if the aforementioned requirement of which conformity is assessed with any of the shapes it may assume is fulfilled. With such location of the second cushion sensor SC2 as described above, the upward/downward motion of the thighs of the occupant P can be detected properly by the second cushion sensor SC2.

As shown in FIG. 2 and FIG. 3 (a), the seat back S2 has the pressure sensors PS4 to PS6 provided thereat. The pressure sensors PS4 are provided in positions corresponding to the back of the lumbar region of the occupant P. The pressure sensors PS4 may be located, for example, in positions 45 to 55 mm, e.g., 50 mm, apart from the laterally central position C of the vehicle seat S to the left and to the right.

The pressure sensors PS5 are located a little above the pressure sensors PS4, and may be located, for example, in positions 70 to 80 mm, e.g., 75 mm, apart from the pressure sensors PS4 above, and 85 to 95 mm, e.g., 90 mm, apart from the central position C to the left and to the right. The pressure sensors PS4 and the pressure sensors PS5 are an example of a first back sensor provided at the seat back S2 and located in a lower position thereof. The first back sensor comprises at least one right back sensor (pressure sensors PS4, PS5) and at least one left back sensor (pressure sensors PS4, PS5).

The pressure sensors PS4 and the pressure sensors PS5 are both intended for measurements of pressure from the lumbar region of an occupant P, and only providing either of the pressure sensors PS4 or PS5 may also be appropriate. Therefore, in the description that follows, the pressure sensors PS4 and the pressure sensors PS5 are also referred to collectively as a first back sensor SB1 for convenience' sake.

The pressure sensors PS6 are located above and distanced far from the pressure sensors PS4 and the pressure sensors PS5. The pressure sensors PS6 are an example of a second back sensor provided at the seat back S2 and located farther above the first back sensor SB1. In the description that follows, the pressure sensors PS6 are also referred to as a second back sensor SB2.

The pressure sensors PS6 are located in positions corresponding to the upper region of the back of the occupant P, and allowed to measure values of pressure from the scapulae of the occupant P. The pressure sensors PS6 may be located 190 to 210 mm, e.g., 200 mm, above the pressure sensors PS5 (i.e., 275 mm above the pressure sensors PS4), and 95 to 105 mm, e.g., 100 mm, apart from the central position C to the left and to the right.

As shown in FIG. 4, the second back sensor SB2 may preferably be located above a position E2 distanced 300 mm upward from the seat surface F1 of the seat cushion S1 as measured along the seat surface SF2 of the seat back S2. It is to be understood that the first back sensor SB1 is located below the position E2. The position E2 as mentioned herein is measured by placing one arm M21 of an L-shaped framing square M2 on the seat surface SF2 of the seat back S2, bringing the other arm M22 into contact with the seat surface SF1 of the seat cushion S1, and reading the scale of the arm M21. In embodiments where the seat back S2 has an adjustable shape (e.g., with lumbar supports), it will suffice if the aforementioned requirement of which conformity is assessed with any of the shapes it may assume is fulfilled. With such location of the second back sensor SB2 as described above, the pressure received from the shoulders of the occupant P can be detected by the second back sensor SB2.

In the following description, pressure values acquired by the pressure sensors PS1 to PS6 are indicated with P1 to P6, and the pressure values of the right and left sensors are indicated with subscripts R and L as $P1_R$, $P1_L$. The pressure sensors PS1 to PS6 are each configured, for example, as an element whose electrical resistance varies with external pressure applied thereto, wherein the larger the pressure value, the higher (or the lower, as the case may be) the voltage of the detection signal becomes. Accordingly, in practical applications, the magnitude of the pressure values are compared with reference made to the magnitude of the voltage values; however, for easy understanding, this specification is described as if determination is made based on the magnitude of the pressure values.

As shown in FIG. 5, the control unit 100 comprises a measurement value acquisition unit 110, a processing unit 120, a communication unit 130, and a storage unit 190. The control unit 100 includes a CPU, a ROM, a RAM, a rewritable nonvolatile memory, etc.; each functional unit is implemented through execution of pre-stored programs.

The control unit 100 is connected to a near-field communication device 3A which enables a near-field communication, such as Bluetooth (registered trademark), Wi-Fi (registered trademark), etc. The control unit 100 is capable of communicating with the smartphone SP via the communication unit 130 and the near-field communication device 3A, and configured to cooperate with apps (applications) installed in the smartphone SP to provide predetermined screens or voices/sounds to the smartphone SP, and allowed to acquire data entered via the smartphone SP.

The measurement value acquisition unit 110 has a function of acquiring measurement values of pressure per predetermined control cycle from the respective pressure sensors PS1 to PS6. The measurement values acquired by the measurement value acquisition unit 110 are stored in the storage unit 190 and used in the processing unit 120. The storage unit 190 is used to store data required for computation, processing, etc., on an as-appropriate basis.

The processing unit 120 is a unit for providing a physical exercise game to an occupant P via the smartphone SP, and configured to execute a general process of the proceeding of the game in accordance with pre-stored programs. The processing unit 120 comprises a motion instruction unit 121 and a motion determination unit 122.

The motion instruction unit 121 is a unit for instructing an occupant P to do a predetermined motion. In the present embodiment, motions to be instructed are pre-stored for respective menu options of the physical exercise game. For example, the menu options of the physical exercise game include a whole-body course and a lower-body course; for the whole-body course, a series of motions are stored in a motion list as shown in FIG. 7. In this motion list, motion codes MC and associated durations [ms] during which the relevant motions are to be done are stored in conjunction with the sequence "No." of the motions. For example, to the first motion "No. 1" is assigned a motion code "1R" with a duration of 1000 ms, and to the next motion "No. 2" is assigned a motion code "1L" with a duration of 1000 ms, such being stored therein. The denotation of the respective motion codes are shown in FIG. 6: "1R" and "1L" denote heel lift motions; "2R" and "2L" denote foot lift motions; "3" denotes a sit-up-straight motion; "4" denotes a scapulae press motion; and "5R" and "5L" denote upper-body turn motions. R and L suffixed in some codes denote the motions at/to the right and at/to the left, respectively; for example, "1R" denotes a right-foot heel lift motion, and "5L" denotes an upper-body turn (twist)-left motion.

In the motion list shown in FIG. 7, the motion code "0" of No. 301 denotes no motion to be done, and "EOL" denotes the end of the motion list.

Instructions to do motions in accordance with the motion list are given by the motion instruction unit 121 which reads out, and outputs to the app of the smartphone SP, the motion codes MC and the durations, sequentially in ascending order of the No. of the motion list. The app of the smartphone SP uses image data and voice/sound data associated with the motion codes MC and stored therein, and outputs images (including time-varying images, or animation) containing text on the screen of the smartphone SP, and music and voice from the speaker(s) of the smartphone SP, and thereby outputs instructions on motions (i.e., by means of sound, light, image, moving image, and textual characters).

Hereafter, a description will be given of each motion.

The heel lift motion refers to an exercise of lifting a heel up from the floor. The heel lift motion includes a calf exercise of exercising a calf to lift a heel up with a tiptoe kept on the floor, and a foot lift exercise of mainly exercising a femoral muscle and a iliopsoas muscle to lift the tiptoe as well up from the floor. This is because both of these motions cause a heel to lift up.

It is to be understood that in the present embodiment, which shows an exemplified configuration in which the motion instruction unit 121 discriminatively instructs two exercises of the calf exercise and the foot lift exercise, the heel lift exercise thus denotes only the calf exercise (which should, in the narrower sense of the term, only be referred to as heel lift exercise). For example, the calf exercise herein is presented in the app as "Lift your heel up". On the other hand, in other embodiments which implement a configuration in which the instruction is not discriminatively given to perform these two exercises of the calf exercise and the foot lift exercise, the heel lift exercise may refer to the both of the calf exercise and the foot lift exercise (the heel lift exercise defined in the broader sense of the term). The following description of the heel lift exercise will be given with an appropriate supplemental remark as to whether it is used in the narrower sense or in the broader sense.

The foot lift motion refers to an exercise of lifting a foot up apart from the floor.

The sit-up-straight motion refers to an exercise of pulling the back upright to keep the back apart from the seat back S2.

The scapulae press motion refers to an exercise of pressing scapulae against the seat back S2.

The upper-body turn motion refers to an exercise of turning (twisting) the upper body right or left while sitting on the seat cushion S1, which is performed by consciously attempting to turn his/her face sideways or backward. Attention should be given that the upper body being twisted should be kept in contact with the seat back S2. For example, the turn-right motion should be performed with the right shoulder being kept in contact with the seat back S2 while the left shoulder getting off from the seat back S2.

If the motion determination unit 122 determines that an occupant P is not doing a predetermined motion instructed by the motion instruction unit 121, the motion instruction unit 121 then gives the instruction again to do the predetermined motion.

In the present embodiment, the motion determination unit 122 sets a motion determination code MCJ indicative of the result of motion determination at 0 if it fails to identify the motion, as will be described later; therefore, the motion instruction unit 121 responds to the result of MCJ=0 and gives an instruction again to do a predetermined motion (the motion corresponding to the data retrieved from the motion list) via the smartphone SP.

The message to be outputted by the motion instruction unit 121 to the smartphone SP if an occupant P is not doing a predetermined motion instructed by the motion instruction unit 121 is stored in the storage unit 190. Such messages are associated with the corresponding motion codes MC as shown in FIG. 8, and thus different messages are stored, respectively.

If the motion determination unit 122 determines that the predetermined motion the occupant P is doing is deficient in scale, the motion instruction unit 121 then gives the occupant P an instruction to do the predetermined motion on a larger scale.

In the present embodiment, the motion determination unit 122 sets a scale data item MS indicative of the scale of the motion at 2 if the motion is sufficient, at 1 if the motion is deficient, and at 0 if no motion is detected, as will be described later; therefore, the motion instruction unit 121 responds to the resulting scale data item MS being set at 1, and gives the occupant P an instruction to do the predetermined motion on a larger scale via the smartphone SP.

The message to be outputted by the motion instruction unit 121 to the smartphone SP if the predetermined motion the occupant P is doing is deficient in scale is stored in the storage unit 190. Such messages are associated with the corresponding motion codes MC as shown in FIG. 9, and thus different messages are stored, respectively.

If the motion determination unit 122 determines that a motion the occupant is doing is different from the motion instructed by the motion instruction unit, the motion instruction unit 121 then notifies the occupant P of a proper way to do the motion.

In the present embodiment, if the motion code MC as instructed and the motion determination code MCJ fail to match, the motion determination unit 122 then notifies the occupant P of a proper way to do the motion via the smartphone SP.

The message to be outputted by the motion instruction unit 121 to the smartphone SP if the motion the occupant P is doing is different from the motion instructed by the motion instruction unit 121 is stored in the storage unit 190. Such messages are associated with the corresponding combinations of the motion codes MC and the motion determination codes MCJ as shown in FIG. 10, and thus different messages are stored, respectively.

The motion determination unit 122 is configured to identify the motion of the occupant P based on outputs of at least two pressure sensors PS1 to PS6 of the first cushion sensor SC1, the second cushion sensor SC2, the first back sensor SB1, and the second back sensor SB2. The motion determination unit 122 makes a determination, after the motion instruction unit 121 gives an instruction to do a predetermined motion, as to whether or not an occupant P is doing the predetermined motion.

In FIG. 6, the criteria for determination of motion is tabulated and shown in detail. To be more specific, the motion determination unit 122 makes evaluations of pressure values with respect to those acquired when a reference posture is assumed, and if the pressure value P2 of the pressure sensor PS2 of the first cushion sensors SC1 at a lifted foot side goes up and the pressure value P3 of the pressure sensor PS3 of the second cushion sensor SC2 at the same side goes down, then determines that the heel lift motion has been done.

The reference posture here refers to a posture assumed by an occupant P in a normal seated state with his/her upper body rested on the back, his/her foots unraised and the upper body untwisted; average pressure values as acquired by the pressure sensors PS1 to PS6 when the occupant P is in this state are stored in the storage unit 190. Pressure values to be stored as those acquired when the reference posture is assumed by an occupant P may be understood to be values of pressure from an average adult, or pressure values acquired when the reference posture is assumed may be stored for weights of such occupants P. Herein, for the sake of simplicity, it is assumed that one pressure value is stored for each of the pressure values as acquired when a representative reference posture is assumed, for example, by an average adult.

It is also to be understood that such a representation as SC1 (PS2) in FIG. 6 means that the measurement values of the pressure sensors PS2, among the two pairs of pressure sensors PS1, PS2 (the total four sensors if the left and right sensors are reckoned in) of the first cushion sensors SC1, are used for evaluations. In the present embodiment, for example, when determination is made as to the heel lift motion, the measurement values of the pressure sensors PS2 are used as the first cushion sensors SC1, but the measurement values of the pressure sensors PS1 may be used, instead. For the other motions as well, if the motion determination is made based on the measurement values of the first cushion sensors SC1, either of the measurement values of the two sets of pressure sensors PS1 or PS2 may be used. Similarly, if the motion determination is made based on the measurement values of the first back sensors SB1, either of the measurement values of the two sets of pressure sensors PS4 or PS5 may be used.

The motion determination unit 122 makes evaluations of pressure values with respect to those acquired when the reference posture is assumed, and if the pressure value P2 and the pressure value P4 of the pressure sensor PS2 and the pressure sensor PS5 of the first cushion sensors SC1 and the first back sensors SB1, respectively, which are values of pressure at a lifted foot side, go up and the pressure value P3 of the second cushion sensor SC2 at the same side goes down, then determines that a foot lift motion has been done. In the present embodiment, to insure higher accuracy, the conditions on which the motion is identified as the foot lift motion are restricted by further requiring that the pressure value P6 of the second back sensor SB2 at the laterally opposite side goes down.

The motion determination unit 122 makes evaluations of pressure values with respect to those acquired when the reference posture is assumed, and if the pressure values P1 of the pressure sensors PS1 of the first cushion sensors SC1 go up and the pressure values P5 of the pressure sensors PS5 of the first back sensors SB1 go down, then determines that a sit-up-straight motion has been done. In the present embodiment, to insure higher accuracy, the conditions on which the motion is identified as the sit-up-straight motion are restricted by further requiring that the pressure values P6 of the second back sensors SB2 go down.

It is to be understood that the sit-up-straight motion is exercised without distinction between the left and the right; therefore, the sum of pressure values at the left and at the right are used herein.

The motion determination unit 122 makes evaluations of pressure values with respect to those acquired when the reference posture is assumed, and if the pressure values P1 of the pressure sensors PS1 of the first cushion sensors SC1 and the pressure values P6 of the second back sensors SB2 go up and the pressure values P4 of the pressure sensors PS4 of the first back sensors SB1 go down, then determines that a scapulae press-against-seat-back motion has been done.

It is to be understood that the scapulae press-against-seat-back motion is exercised without distinction between the left and the right; therefore, the sum of pressure values at the left and at the right are used herein.

The motion determination unit 122 makes evaluations of pressure values with respect to those acquired when the reference posture is assumed, and if the pressure value $P1_R$ of the pressure sensor PS1 of the right first cushion sensors SC1 and the pressure value $P4_R$ of the pressure sensor PS4 of the right first back sensors SB1 go up and the pressure value $P4_L$ of the pressure sensor PS4 of the left first back sensors SB1 and the pressure value $P6_L$ of the left second back sensor SB2 go down, then determines that an upper-body turn-right motion has been done, while if the pressure value $P1_L$ of the pressure sensor PS1 of the left first cushion sensors SC1 and the pressure value $P4_L$ of the pressure sensor PS4 of the left first back sensors SB1 go up and the pressure value $P4_R$ of the pressure sensor PS4 of the right first back sensors SB1 and the pressure value $P6_R$ of the right second back sensors SB2 go down, then determines that an upper-body turn-left motion has been done.

Determination described above as to whether the pressure value goes up or goes down with respect to that acquired when the reference posture is assumed may be carried out by comparison made with their threshold values stored beforehand in the storage unit 190.

For each motion, the scale of the motion can be determined by comparison made between the pressure value and a predetermined threshold value. The motion determination unit 122 sets a scale data item MS at 2 if the motion is sufficient in scale, at 1 if the motion is deficient, and at 0 if no motion is detected.

Next, referring to FIG. 11 to FIG. 15, one example of the process for providing a physical exercise game is described.

Figure 11:
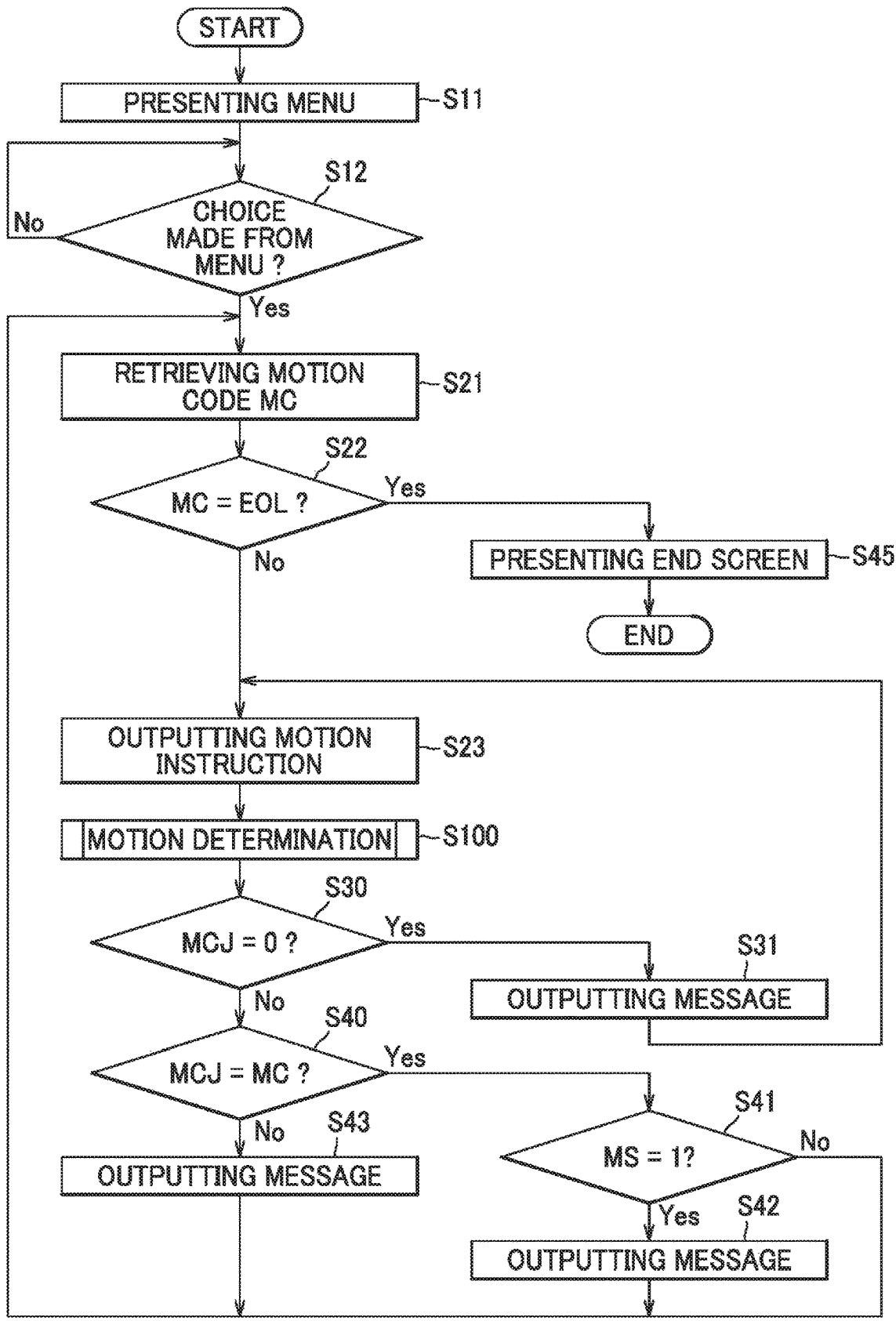
FIG. 11 is a flowchart showing an example of a process of a control unit.
Figure 12:
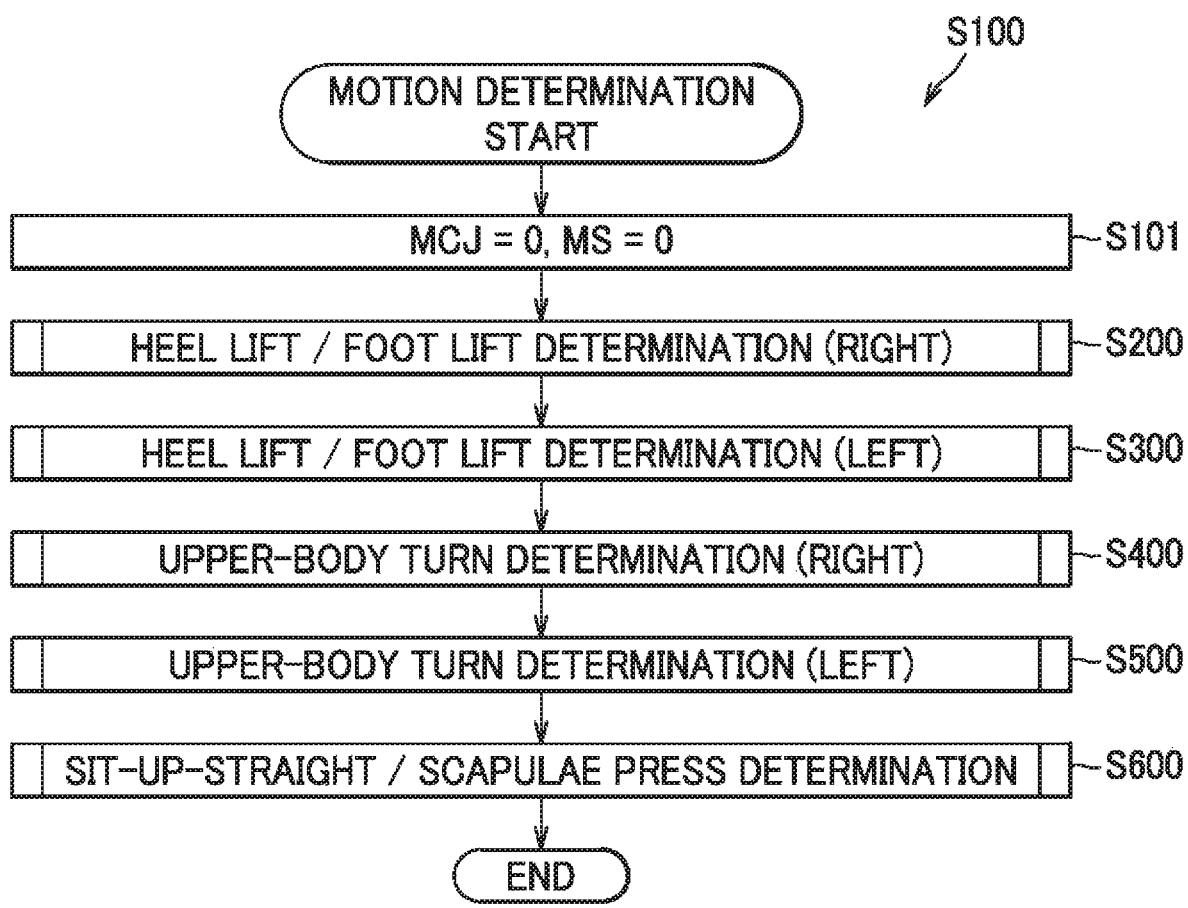
FIG. 12 is a flowchart of a process for determination of motions.
Figure 16:
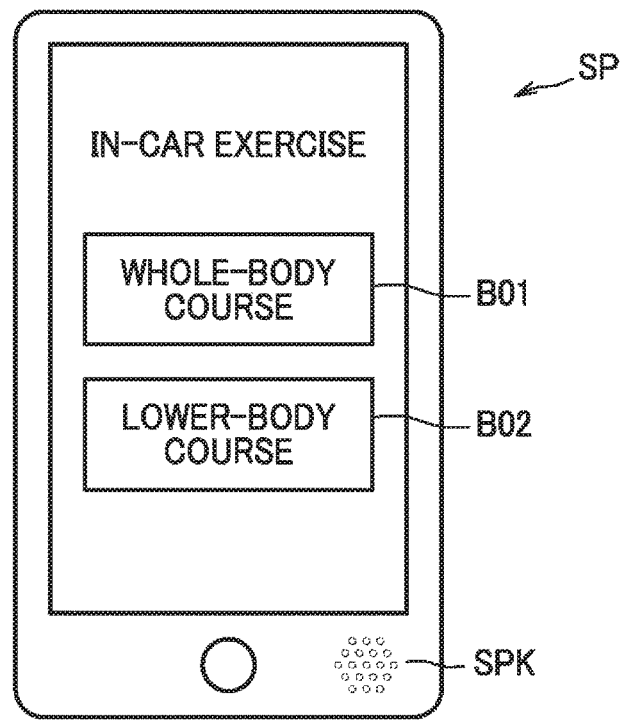
FIG. 16 is an example of a menu screen.

As shown in FIG. 11, the processing unit 120 presents a menu screen for the physical exercise game at the smartphone SP (S11). In the menu screen, for example, as shown in FIG. 16, the "whole-body course" button B01 and the "lower-body course" button B02 are presented as options of an in-car physical exercise menu to prompt an occupant P to make a choice therebetween. The processing unit 120 determines whether or not a choice has been made from the menu (a signal that a relevant button has been touched has been received) and waits until a choice is made (No, S12).

Figure 17:
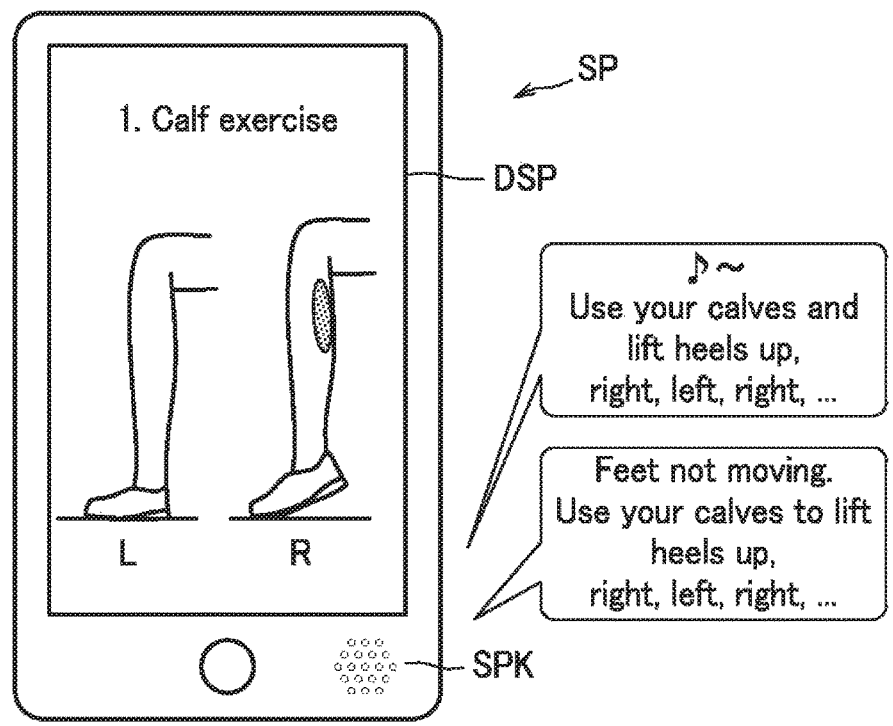
FIG. 17 is an example of a screen for a calf exercise.

If the occupant P touches the button B01 or the button B02 to make a choice from the menu (Yes, S12), the processing unit 120, i.e., the motion instruction unit 121, then retrieves a motion code MC from the motion list (S21), and determines whether the motion code MC is "EOL" or not (S22). If the motion code MC is not "EOL" (No, S22), the motion instruction unit 121 then outputs the retrieved motion code MC and motion time (duration) to the smartphone SP as a motion instruction (S23). According to this motion instruction, the smartphone SP issues instructions by showing, for example, a text instruction "1. Calf exercise" and an image (animation or other moving image) corresponding to the motion code MC as shown in FIG. 17 on the display DSP, and by generating voices/sounds such as "Use your calves and lift heels up, right, left, right, . . . " from the speaker SPK. At the same time, music in rhythm with the motion time may be outputted so that the occupant P can work out to the rhythm. Here, in FIG. 17, a legend showing the calf exercise (heel lift exercise in the narrower sense of the term) and an image showing the right heel lifted up are displayed by way of example.

Then, the motion determination unit 122 determines the motion of the occupant P based on the pressure values acquired from the pressure sensors PS1 to PS6 (S100). The process of determining the motion starts with initialization in which the motion determination code MCJ and the scale data item MS are both set at 0 (S101).

Subsequently, the heel lift/foot lift determination (right) process (step S200) is executed.

Figure 13:
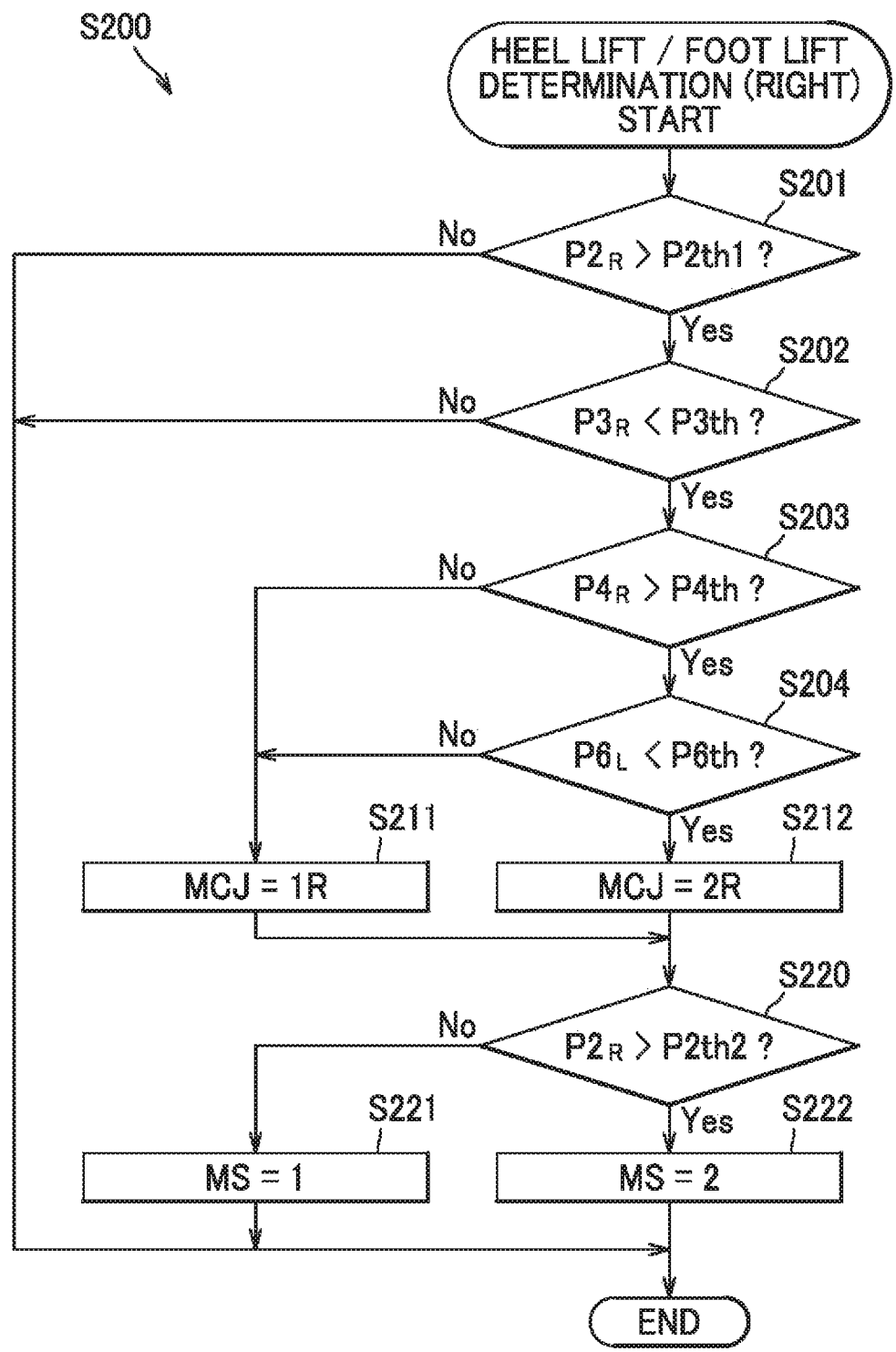
FIG. 13 is a flowchart of a process for determination of heel lift/foot lift motion (right).

In this determination process, as shown in FIG. 13, a determination is made, first, as to whether or not the pressure value $P2_R$ of the right pressure sensor PS2 is greater than a threshold value P2th1 (S201). If the pressure value $P2_R$ is greater than the threshold value P2th1 (Yes, S201), then a determination is made as to whether or not the pressure value $P3_R$ of the right pressure sensor PS3 is smaller than a threshold value P3th (S202). If the pressure value $P3_R$ is smaller than the threshold value P3th (Yes, S202), then it is shown that the pressure under the right buttock goes up while the pressure under the thigh goes down, and the situation thus assessed is that the right heel is lifted up in the broader sense (the heel is lifted regardless of whether or not the foot is on the floor). If the determination in step S201 or step S202 is turned out to result in No, then it is shown that neither the heel lift (in the narrower sense) nor foot lift motion is made; thus, the step S200 comes to an end. In this situation, the motion determination code MCJ and the scale data item MS both remain 0.

After the determination made results in Yes in step S202, the motion determination unit 122 makes a determination as to whether or not the pressure value $P4_R$ of the right pressure sensor PS4 is greater than a threshold value P4th, and if greater (Yes, S203), then further makes a determination as to whether or not the pressure value $P6_L$ of the left pressure sensor PS6 is smaller than a threshold value P6th (S204).

If the pressure value $P6_L$ is smaller than the threshold value P6th (Yes, S204), then it is shown that the foot is taken off the floor whereby the right lumbar region is pressed against the seat back S2 and the left shoulder tends to become separated from the seat back S2; therefore, it is determined that a foot lift exercise is being done. Accordingly, the motion determination code MCJ is set at 2R (right foot lift exercise) (S212). On the other hand, if the determination made in step S203 or step S204 results in No, then it is assumed that the foot is not taken off the floor; accordingly, the motion determination code MCJ is set at 1R (right heel lift exercise) (S211).

After step S211 or step S212, the motion determination unit 122 makes a determination as to whether or not the pressure value $P2_R$ of the right pressure sensor PS2 is greater than a threshold value P2th2 (S220). Herein, it is to be understood that the threshold value P2th1 is a value for determining whether an exercise being made can be evaluated, to say the least, as a heel lift motion or not, and the threshold value P2th2 is a value for determining whether the heel is lifted up sufficiently or not. In short, P2th2 is greater than P2th1.

If the pressure value $P2_R$ is greater than the threshold value P2th2 (Yes, S220), then it is assumed that the exercise being made is sufficient in scale; thus, the scale data item MS is set at 2 (S222). On the other hand, if the pressure value $P2_R$ is not greater than the threshold value P2th2 (No, S220), then it is assumed that the motion is deficient in scale; thus, the scale data item MS is set at 1 (S221).

Up to this point, the heel lift/foot lift determination (right) process step S200 comes to an end; subsequently, referring back to FIG. 12, a heel lift/foot lift determination (left) process step S300 is executed. Since step S300 differs from step S200 only in that pressure values are determined at reversed locations, right or left, an explanation thereof will be omitted.

After step S300, an upper-body turn determination (right) process step S400 is executed.

Figure 14:
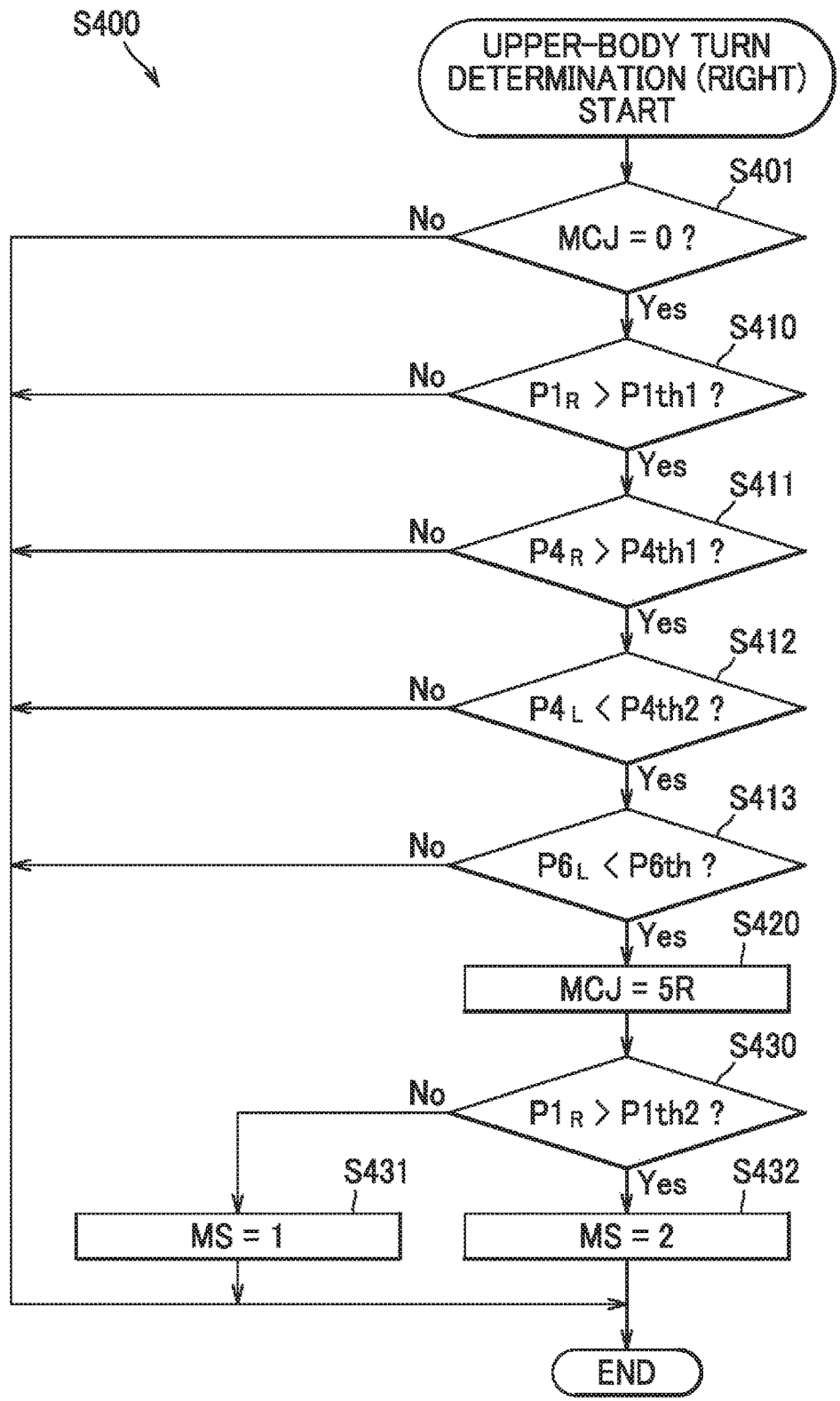
FIG. 14 is a flowchart of a process for determination of upper-body turn motion (right).

As shown in FIG. 14, first, a determination is made as to whether the motion determination code MCJ is 0 or not (S401). If MCJ is not 0 (No, S401), then it is shown that the motion determination has already been completed; thus, step S400 comes to an end.

If MCJ is 0 (Yes, S401), then a determination is made as to whether or not the pressure value $P1_R$ of the right pressure sensor PS1 is greater than a threshold value P1th1 (S410). If the pressure value $P1_R$ is greater than the threshold value P1th1 (Yes, S410), then an additional determination is made as to whether or not the pressure value $P4_R$ of the right pressure sensor PS4 is greater than a threshold value P4th1 (S411). If the pressure value $P4_R$ is greater than the threshold value P4th1 (Yes, S411), then a further determination is made as to whether or not the pressure value $P4_L$ of the left pressure sensor PS4 is smaller than a threshold value P4th2 (S412). Herein, P4th2 is a value smaller than P4th1. If the pressure value $P4_L$ is smaller than the threshold value P4th2 (Yes, S412), then a further determination is made as to whether or not the pressure value $P6_L$ of the left pressure sensor PS6 is smaller than a threshold value P6th (S413). If the pressure value $P6_L$ is smaller than the threshold value P6th (Yes, S413), then it is assumed that the upper body is turned right; accordingly, the motion determination code MCJ is set at 5R (S420). On the other hand, if any of the steps S410, S411, S412, S413 results in No, then it is assumed that the upper body is not turned right; accordingly, the motion determination code MCJ and the scale data item MS are not changed, and step S400 comes to an end.

After the motion determination code MCJ is set at 5R, the motion determination unit 122 makes a determination as to whether or not the pressure value $P1_R$ is greater than a threshold value P1th2 (S430). Herein, it is to be understood the threshold value P1th1 is a value for determining whether an exercise being made can be evaluated, to say the least, as an upper-body turn motion or not, and the threshold value P1th2 is a value for determining whether the upper body is turned sufficiently or not. In short, P1th2 is greater than P1th1.

If the pressure value $P1_R$ is greater than the threshold value P1th2 (Yes, S430), then it is assumed that the exercise being made is sufficient in scale; thus, the scale data item MS is set at 2 (S432). On the other hand, if the pressure value $P1_R$ is not greater than the threshold value P1th2 (No, S430), then it is assumed that the motion is deficient in scale; thus, the scale data item MS is set at 1 (S431).

Up to this point, the upper-body turn determination (right) process step S400 comes to an end; subsequently, referring back to FIG. 12, an upper-body turn determination (left) process step S500 is executed. Since step S500 differs from step S400 only in that pressure values are determined at reversed locations, right or left, an explanation thereof will be omitted.

After step S500, a sit-up-straight/scapulae press determination process step S600 is executed.

Figure 15:
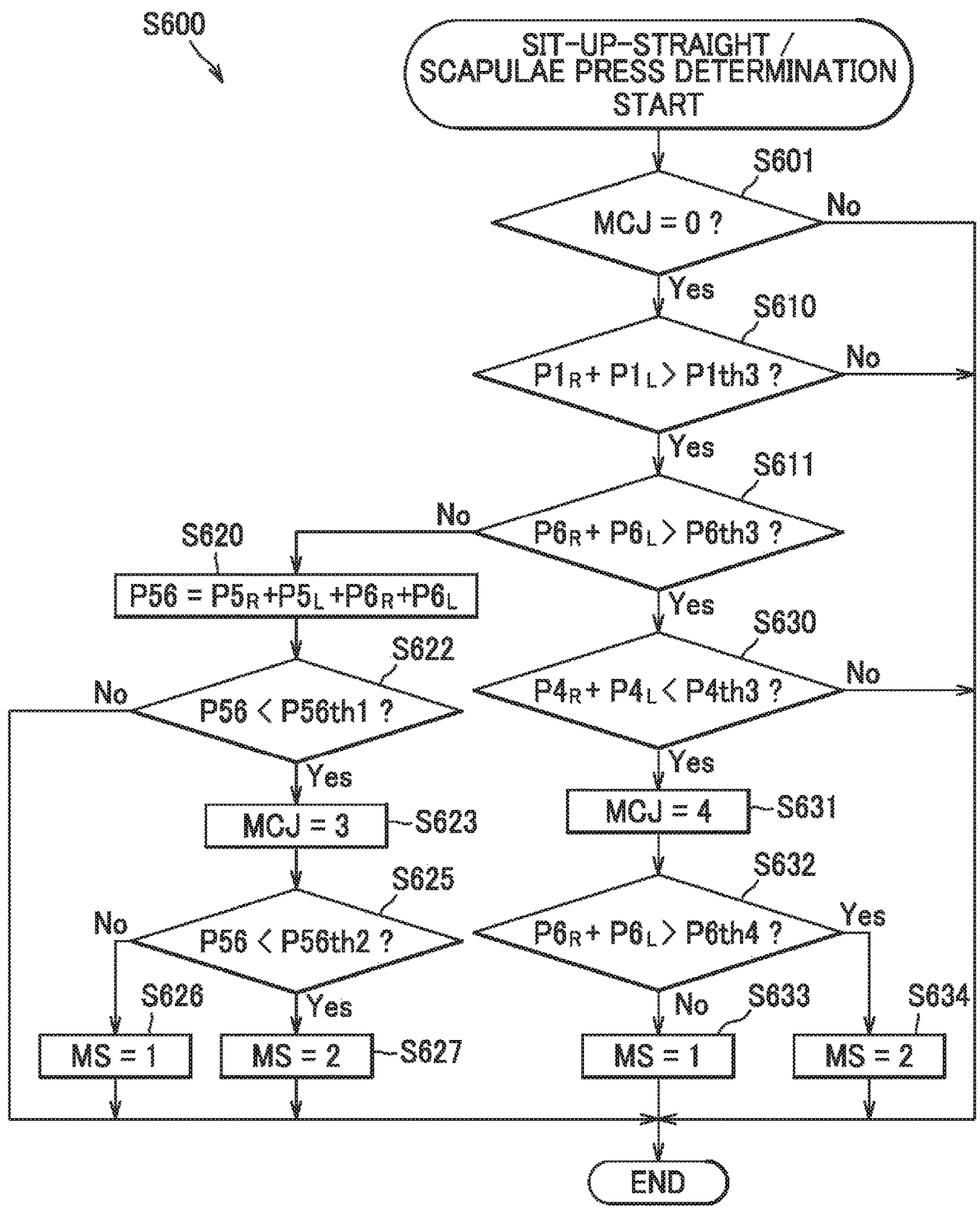
FIG. 15 is a flowchart of a process for determination of sit-up-straight/scapulae press motion.

As shown in FIG. 15, first, a determination is made as to whether the motion determination code MCJ is 0 or not (S601). If MCJ is not 0 (No, S601), then it is shown that the motion determination has already been completed; thus, step S600 comes to an end.

If MCJ is 0 (Yes, S601), a determination is made as to whether the sum of the pressure value $P1_R$ of the right pressure sensor PS1 and the pressure value $P1_L$ of the left pressure sensor PS1 is greater than a threshold value P1th3 (S610). If the sum of the pressure value $P1_R$ and the pressure value $P1_L$ is not greater than the threshold value P1th3 (No, S610), then it is assumed that neither the sit-up-straight motion nor the scapulae press motion has been done; thus, step S600 comes to an end. In this situation, the motion determination code MCJ and the scale data item MS are both 0, and it is determined that no motion has been done. If the sum of the pressure value $P1_R$ and the pressure value $P1_L$ is greater than the threshold value P1th3 (Yes, S610), then a further determination is made as to whether the sum of the pressure value $P6_R$ of the right pressure sensor PS6 and the pressure value $P6_L$ of the left pressure sensor PS6 is greater than a threshold value P6th3 (S611).

If the sum of the pressure value $P6_R$ of the right pressure sensor PS6 and the pressure value $P6_L$ of the left pressure sensor PS6 is not greater than the threshold value P6th3 (No, S611), then it is assumed that the scapulae are not pressed against the seat back S2; therefore, the motion determination unit 122 computes the sum P56 of the pressure values $P5_R$, $P5_L$ of the right and left pressure sensors PS5 and the pressure values $P6_R$, $P6_L$ of the right and left pressure sensors PS6 to make a determination as to whether or not the sit-up-straight motion has been done (S620). Then, a determination is made as to whether or not P56 is smaller than a threshold value P56th1 (S622). If P56 is not smaller than the threshold value P56th1 (No, S622), the upper body is not so sufficiently apart from the seat back S2 that the occupant can be assumed to be sitting up straight; accordingly, the motion determination code MCJ and the scale data item MS both remain unchanged at 0, and step S600 comes to an end.

On the other hand, in step S622, if P56 is smaller than the threshold value P56th1 (Yes, S622), then the upper body is apart sufficiently from the seat back S2 to such an extent that the occupant can be assumed to be sitting up straight; accordingly, the motion determination code MCJ is set at 3 (S623).

Subsequently, the motion determination unit 122 makes a determination as to whether or not P56 is smaller than a threshold value P56th2 (S625). Herein, the threshold value P56th2 is a value smaller than P56th1. If P56 is not smaller than the threshold value P56th2 (No, S625), then it is assumed that the occupant's back slightly pushes the seat back S2, and thus the motion is deficient; therefore, the scale data item MS is set at 1 (S626). On the other hand, if P56 is smaller than the threshold value P56th2 (Yes, S625), then it is assumed that the occupant's back is separated sufficiently apart from, or nearly fails to push the seat back S2 and thus the motion is sufficient; accordingly, the scale data item MS is set at 2 (S627). After step S626 and step S627, step S600 comes to an end (Step 627).

In step S611, if it is determined that the sum of the pressure value P6$_R$ and the pressure value P6$_L$ is greater than the threshold value P6*th*3 (Yes, S611), then it is assumed that the scapulae are pressed against the seat back S2 to some extent; accordingly, the motion determination unit 122 further makes a determination as to whether or not the sum of the pressure value P4$_R$ of the right pressure sensor PS4 and the pressure value P4$_L$ of the left pressure sensor PS4 is smaller than a threshold value P4*th*3 (S630).

If the sum of the pressure value P4$_R$ and the pressure value P4$_L$ is not smaller than the threshold value P4*th*3 (No, S630), then it is assumed that the occupant's back in its entirety rather than his/her scapulae is pressed against the seat back S2; accordingly, the motion determination code MCJ and the scale data item MS both remain unchanged at 0, and step S600 comes to an end.

If the sum of the pressure value P4$_R$ and the pressure value P4$_L$ is smaller than the threshold value P4*th*3 (Yes, S630), then it is assumed that not the occupant's back in its entirety but his/her scapulae are successfully pressed against the seat back S2; accordingly, the motion determination code MCJ is set at 4 (S631).

Next, a determination is made as to whether or not the sum of the pressure value P6$_R$ and the pressure value P6$_L$ is greater than a threshold value P6*th*4 (S632). The threshold value P6*th*4 is a value for determining whether or not it can be assumed that the scapulae are pressed hard sufficiently against the seat back S2, and assumes a value greater than the threshold value P6*th*3. If the sum of the pressure value P6$_R$ and the pressure value P6$_L$ is not greater than the threshold value P6*th*4 (No, S632), then it is assumed that the power pressing the scapulae against the seat back S2 is not sufficient, and the scale data item MS is set at 1 (S633), while if the sum of the pressure value P6$_R$ and the pressure value P6$_L$ is greater than the threshold value P6*th*4 (Yes, S632), then it is assumed that the power pressing the scapulae against the seat back S2 is sufficient, and the scale data item MS is set at 2 (S634); in either case, step S600 comes to an end. Accordingly, the motion determination process step S100 comes to an end.

Referring back to FIG. 11, after the motion determination process step S100, the motion instruction unit 121 makes a determination as to whether or not the motion determination code MCJ is 0 (S30), and if MCJ is 0 (Yes, S30), then outputs a message (S31). Take, as an example, the occasion when a calf exercise proceeds, as shown in FIG. 17, if the motion determination code MCJ is 0, then the motion instruction unit 121 looks up a message table of FIG. 8, retrieves and outputs a message associated with the motion code 1R to the smartphone SP. In response, a message is outputted from the speaker SPK of the smartphone SP, such as "Feet not moving. Use your calves to lift heels up" (see FIG. 17).

After outputting the message, the motion instruction unit 121 returns to step S23, and gives an instruction again to do a predetermined motion.

If it is determined, in step S30, that the motion determination code MCJ is not 0 (No, S30), then the motion instruction unit 121 makes a determination as to whether or not the motion determination code MCJ coincides with the motion code MC (S40). If the motion determination code MCJ coincides with the motion code MC (Yes, S40), then the motion determination unit 122 further makes a determination as to whether or not the scale data item MS is 1 (S41). If the scale data item MS is not 1 (No, S41), i.e., the scale data item MS is 2, then it is assumed that the occupant P is successfully doing a motion as instructed; accordingly, the process goes back to step S21 to give an instruction to do the next motion.

Figure 18:
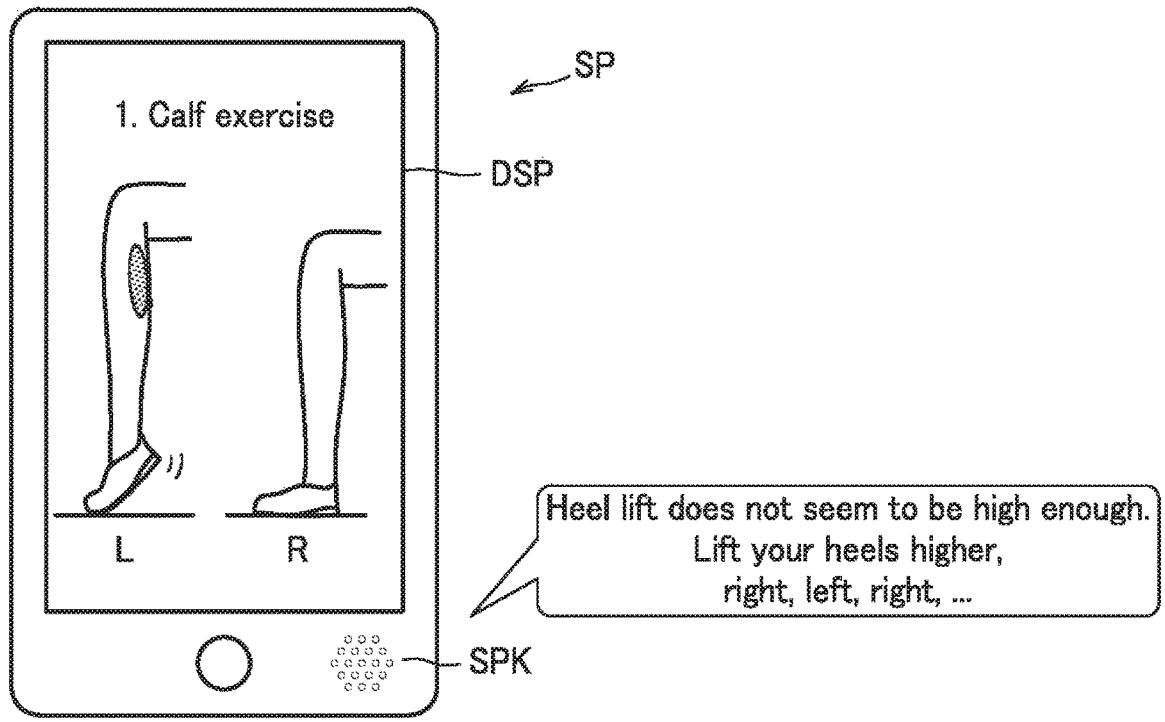
FIG. 18 is an example of a screen presented when the motion is small in scale.

If it is determined, in step S41, that the scale data item MS is 1 (Yes, S41), then it means that the scale of the motion is deficient; accordingly, the motion instruction unit 121 outputs a message to do the motion on a larger scale to the smartphone SP (S42). For example, if the scale of the motion in the calf exercise is deficient, a message table of FIG. 9 is consulted and a message associated with the motion code 1L is retrieved and outputted to the smart phone SP. In response, a message is outputted from the speaker SPK of the smartphone SP, such as "Heel lift does not seem to be high enough. Lift your heels higher. Right, left, right, . . . " as shown in FIG. 18. At this time, an image showing a heel lifted up higher than shown in FIG. 17 may be shown on the display DSP, so as to make it easier for the occupant P to grasp what to do. After the message is outputted, the process goes back to step S21 to give an instruction to do the next motion.

Figure 19:
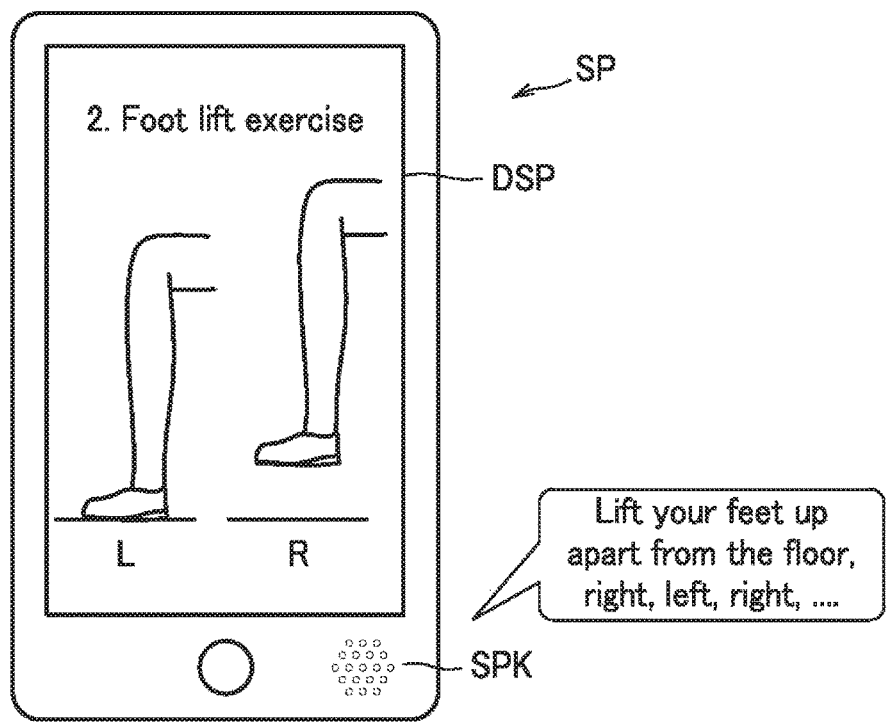
FIG. 19 is an example of a screen presented when it is determined that the motion being done is different from one instructed.

If it is determined, in step S40, that the motion determination code MCJ does not coincide with the motion code MC (No, S40), then it is assumed that the occupant P is doing a motion different from the instructed motion; accordingly, a message advising a proper way to do the motion is outputted to the smartphone SP (S43). For example, if it is determined that a heel up exercise is being done despite the fact that a foot lift exercise is to be done, i.e., with the motion code MC being 2R while the motion determination code MCJ being 1R, then a message associated with a combination of MC being 2R and MCJ being 1R is retrieved from the message table of FIG. 10 and outputted to the smartphone SP. Accordingly, a message as shown in FIG. 19 such as "Lift your feet up apart from the floor. Right, left, right, . . . " is outputted from the speaker SPK of the smartphone SP. After the message is outputted, the process goes back to step S21 to give another instruction to do the next motion.

After the motion code MC is retrieved (S21), if the motion code MC is "EOL" (Yes, S22), then it means that the motion list has reached the bottom; accordingly, the end screen is presented on the smartphone SP or otherwise (S45, illustration thereof omitted), and the process comes to an end.

As described above, in the vehicle seat S according to the present embodiment, the motion of the occupant P can be identified by a combination of pressure values acquired from at least two sensors chosen among at least four sensors of the first cushion sensor SC1 and the second cushion sensor SC2 provided in positions separate from each other in front and behind at the seat cushion S1, and the first back sensor SB1 and the second back sensor SB2 provided in positions separate from each other above and below at the seat back S2.

Also in this vehicle seat S, the control unit 100 can cause the motion instruction unit 121 to give an occupant an instruction to do a motion, and cause the motion determination unit 122 to make a determination as to whether or not the occupant P is doing a predetermined motion after instructed by the motion instruction unit 121 to do the predetermined motion. This makes it possible for the occupant P to do a motion actively and for the vehicle seat S to respond thereto with an evaluation of the quality of that motion; thus, a seat having interactive relationship with an occupant P can be provided. Providing a physical exercise game or the like to encourage an occupant P to do a motion actively as in the embodiment described above could probably serve to relieve fatigue effectively and realize more pleasant journey. Particularly, during long journeys on an airplane or a long-distance bus or other vehicles, which would incur the risk of occurrence of traveler's thrombosis, such traveler's thrombosis could possibly be restrained by such physical exercises taken pleasantly in the vehicle.

With the vehicle seat S according to the present embodiment, values of pressure from an occupant P are acquired; therefore, the motion of the occupant P can be identified precisely.

Since the motion instruction unit 121 responds to a determination made by the motion determination unit 122 that an occupant P is not doing a predetermined motion, and gives a second instruction to do the predetermined motion, the occupant P can be encouraged to do a motion actively.

Since the motion instruction unit 121 responds to a determination made by the motion determination unit 122 that a predetermined motion an occupant P is doing is deficient in scale, and gives the occupant P an instruction to do the predetermined motion on a larger scale, the occupant P can be encouraged to do a larger motion, afforded increased pleasure on the seat, and gifted with a healthy life.

Since the motion instruction unit 121 responds to a determination made by the motion determination unit 122 that a motion an occupant P is doing is different from the motion instructed by the motion instruction unit 121, and notifies the occupant P of a proper way to do the motion, the occupant P can be encouraged to do a health-promoting exercise. Furthermore, in an alternative configuration where the smartphone SP, a navigation system, or other devices are operated in accordance with the motion of an occupant P in contrast to the above-described embodiment implemented as a physical exercise game, the notification of a proper way to do the motion can provide guidance on precise operation.

The first embodiment has been described above, but the present invention is not limited to the above-described embodiment. Specific configurations may be modified where appropriate without departing from the gist of the invention.

For example, although the above-described embodiment is configured such that the motion instruction unit gives an occupant P an instruction to do a predetermined motion by sound, light, image, moving image and textual characters, instructions given by vibrations, and/or warmth or coldness sensation may be feasible. The warmth or coldness sensation herein refers to sensory stimuli of warmth or coldness given to an occupant P; for example, a heater for heating a seat surface or a blower for causing wind to blow against the occupant P may be used to give a stimulus. It is to be understood that the textual characters in the context of this disclosure include Braille characters.

Although the above embodiment is described on the understanding that each of the threshold values assumes a constant value, each threshold value may not be constant. For example, if an occupant can be identified by a smartphone id or the like, the threshold values may be stored for each occupant, whereas the degrees of proficiency and/or habits of each occupant in doing the motions may be assumed and stored in advance, so that the threshold values varying according to his/her degree of proficiency and/or habits may be used for each occupant.

Although the physical exercise game is taken as an example in the above-described embodiment, any other game may be provided. For example, a workout app (as designed to be operated like a game) for realizing an aesthetically pleasing posture can be provided.

Although the control unit mentioned in the above-described embodiment is exemplified by a device other than a smartphone, the control unit may be a combination of a device provided in a seat or a car and a smartphone. To be more specific, the functionalities embodied in the smartphone may be implemented partially or entirely in the components of the seat.

Although the control unit and the smartphone in the above-described embodiment are connected via a radio communication, they may be connected by wire.

Although the pressure value resulting from addition of the left pressure value and the right pressure value is used for the sit-up-straight motion or the like that is to be exercised without distinction between the left and the right in the above-described embodiment, the mean value of the left pressure value and right pressure value may be used as well; alternatively, a determination may be made as to whether the condition is satisfied for each of the right pressure value and the left pressure value, and a determination that the specified motion is being done may be made, if the condition is satisfied for at least one of them, or if the condition is satisfied for the both of them.

In order to identify the motion of an occupant, any measurement values other than pressure values may be acquired. For example, measurement values acquired by capacitance sensors or the like may be used instead.

In the above-described embodiment, a vehicle seat is exemplified by a seat installed in a car, but such a vehicle seat may be a seat installed in a vehicle other than a car, or a seat installed at home, in facilities, or at any other places not in a vehicle.

Second Embodiment

Next, a detailed description of a second embodiment will be given with reference made to the drawings where appropriate.

In the second embodiment, the smartphones SP are not only configured as an example of on-board devices, but also make up a controller in combination with a control unit 100.

In the car CR, provided are a control unit 100, a plurality of seat bodies S0, and smartphones SP which together constitute a system SYS of vehicle seats S. It is to be understood that associations of the smartphones SP for respective occupants P with the corresponding seat bodies S0 are established in advance by means of communications via the control unit 100.

The vehicle seat S in the present embodiment is configured to provide a 100-meter dash game on the smartphone SP as an on-board device. The smartphone SP includes a display DSP (see FIG. 2), and the control unit 100 is configured to respond to an alternate up-and-down motion of left and right legs on the seat body S0, and output a signal for operation causing a character to run a race in the game shown in the display DSP.

Figure 20:
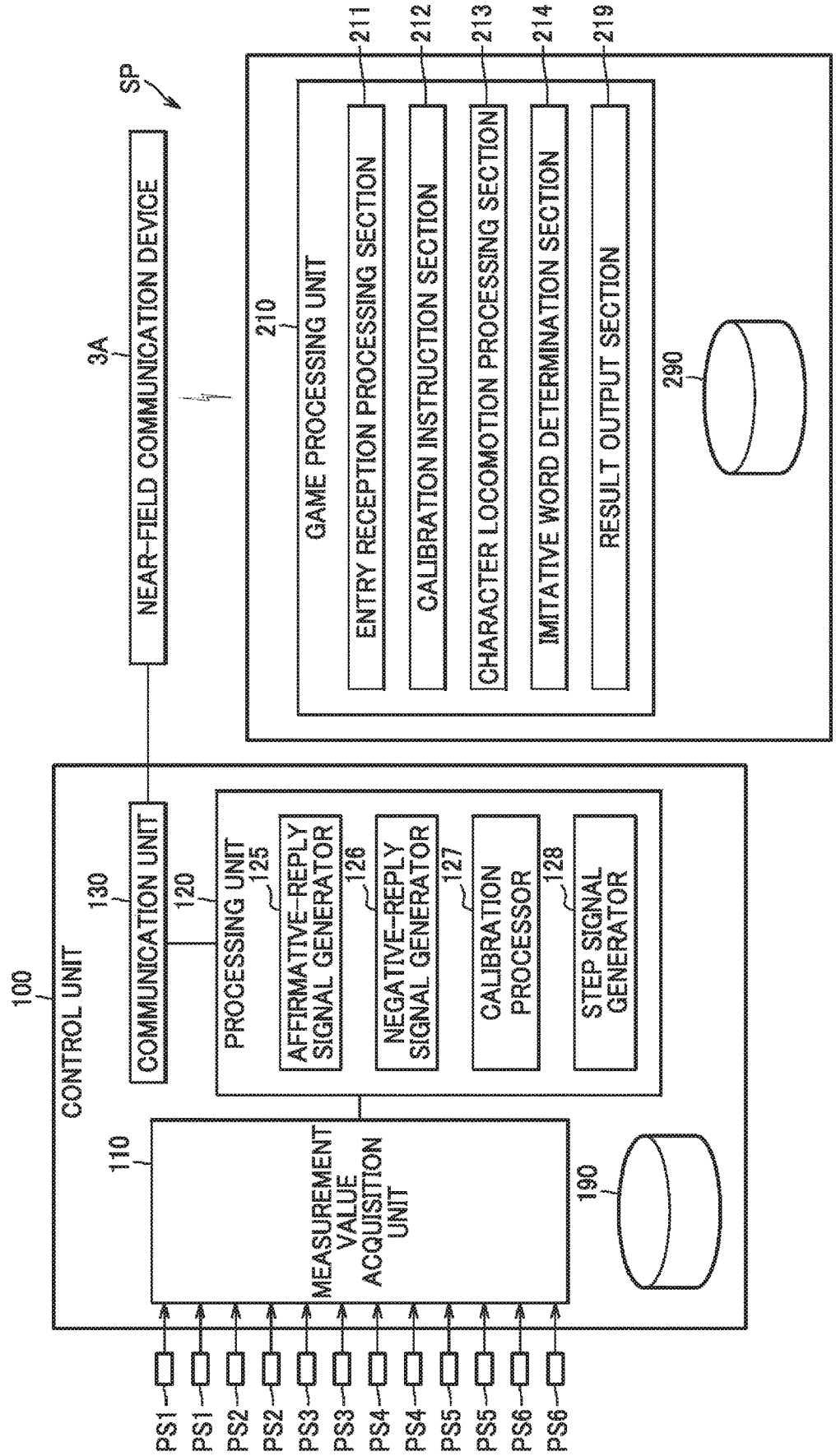
FIG. 20 is a block diagram for explaining a vehicle seat and system configuration according to a second embodiment.

As shown in FIG. 20, the control unit 100 comprises a measurement value acquisition unit 110, a processing unit 120, a communication unit 130, and a storage unit 190. The smartphone SP comprises a game processing unit 210 and a storage unit 290. The control unit 100 and the smartphones SP each include a CPU, a ROM, a RAM, a rewritable nonvolatile memory, etc.; each functional unit is implemented through execution of pre-stored programs.

The control unit 100 is connected to a near-field communication device 3A which enables a near-field communication, such as Bluetooth (registered trademark), Wi-Fi (registered trademark), etc. The control unit 100 is capable of communicating with the smartphone SP via the communication unit 130 and the near-field communication device 3A, and configured to cooperate with apps installed in the smartphone SP to provide predetermined screens or voices/sounds to the smartphone SP, and allowed to acquire data entered via the smartphone SP.

The measurement value acquisition unit 110 has a function of acquiring measurement values of pressure per predetermined control cycle from the respective pressure sensors PS1 to PS6. The measurement values acquired by the measurement value acquisition unit 110 is stored in the storage unit 190 and used in the processing unit 120. The storage unit 190 is used to store data required for computation, processing, etc., on an as-appropriate basis.

The processing unit 120 communicates with the smartphone SP and executes a process of transmitting a signal for operating an app for the 100-meter dash game to be provided in the smartphone SP. The processing unit 120 comprises an affirmative-reply signal generator 125, a negative-reply signal generator 126, a calibration processor 127, and a step signal generator 128.

The processing unit 120 has operation modes which comprise a first operation mode in which a signal is outputted based on the measurement values of the pressure sensors PS1 to PS6, and a second operation mode in which a signal is not outputted. The processing unit 120 may be configured to operate in the first operation mode only after providing notification to prompt an occupant P to do a motion via the smartphone SP. To be more specific, as will be described later, after receipt of a signal indicative of reception of a variety of signals from the smartphone SP, the first operation mode is established to output a signal, while after receipt of a signal indicative of end of reception, the second operation mode is adopted to output no signal.

The affirmative-reply signal generator 125 and the negative-reply signal generator 126 output, to the smartphone SP, an affirmative-reply signal or a negative-reply signal as selected according to the motion of the occupant P, after the processing unit 120 receives an entry reception signal from the smartphone SP.

To be more specific, the affirmative-reply signal generator 125 outputs an affirmative-reply signal on condition that the pressure value $P6_R$ acquired from the right pressure sensor PS6 (first pressure sensor) exceeds a predetermined threshold value P6th. Similarly, the negative-reply signal generator 126 outputs a negative-reply signal on condition that the pressure value $P6_L$ acquired from the left pressure sensor PS6 (second pressure sensor) exceeds a predetermined threshold value P6th.

In the game processing unit 210 of the smartphone SP, to the affirmative-reply signal is assigned a first operation of starting a game for the smartphone SP, and to the negative-reply signal is assigned a second operation of not playing the game.

The calibration processor 127 acquires the pressure values $P3_R$, $P3_L$ from the right and left pressure sensors PS3, after the processing unit 120 receives a calibration start signal from the smartphone SP. Subsequently, the calibration processor 127 determines a normal pressure $P3_n$ that is an average pressure of an occupant P currently seated thereon and a threshold value P3th for detection of peaks of pressure values, and computes and outputs to the smartphone SP a normal step cycle $TS_n$ that is an average time interval in which a sequence of motions of the legs of the occupant P is completed.

Figures 21, 22:
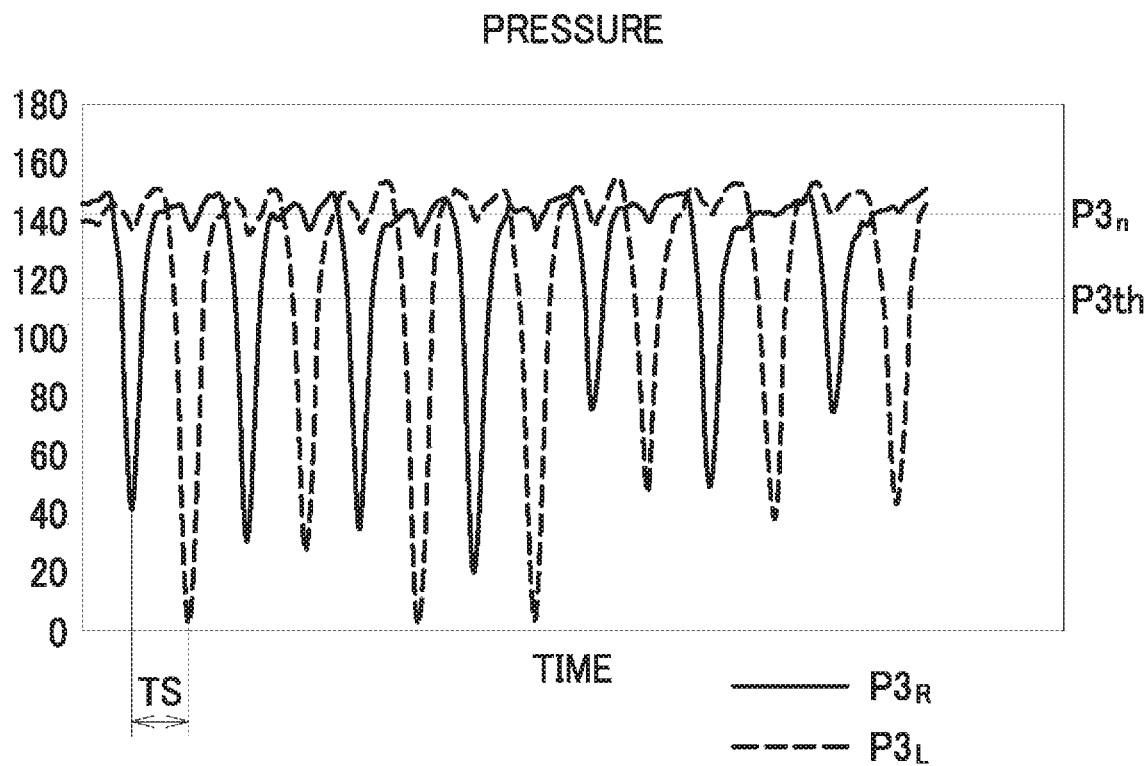
FIG. 21 is a graph showing change of pressure acquired at the time of calibration.
FIG. 22 is a table of criteria for determination of imitative or onomatopoeic words.

To be more specific, when an occupant P lifts his/her legs alternately, the pressure values $P3_R$, $P3_L$ change as shown in FIG. 21, for example. In FIG. 21, a term in which the pressure goes down sharply indicates that the occupant P has lifted his/her leg up and the pressure at an area detected by the pressure sensor PS3 has become small accordingly. In fact, the pressure values that have not gone down but kept at about 140 will be reckoned at an average normal pressure $P3_n$ to be detected when the legs are not lifted up. To compute the normal pressure $P3_n$, for example, you may identify such absolute values as found not greater than a predetermined value (i.e., the values of which variations are small enough) among the absolute values of the differences between the last value and the present value of the pressure values $P3_R$, $P3_L$ (remainders each determined by subtraction of the last value P3(n−1) from the present value P3(n)), and sum up and average the present values from which the identified absolute values are obtained.

The threshold value P3th is a threshold value for determining that the legs are currently being lifted up; for example, as is the case of FIG. 21, values ranging generally from 100 to 120 may be used. For this purpose, the threshold value P3th may be a value obtained by multiplying the normal pressure $P3_n$ by a predetermined value. For example, the value obtained by multiplying the normal pressure $P3_n$ by a predetermined value ranging generally from 0.6 to 0.9 may be feasible for the threshold value P3th.

The normal step cycle $TS_n$ is an average value of the step cycle TS that is a time interval between peaks of the pressure values $P3_R$, $P3_L$.

Peak detection of the pressure values $P3_R$, $P3_L$ may be determined to occur when the difference between the last value and the present value changes from the negative to the positive under the condition that each pressure value $P3_R$, $P3_L$ is smaller than the threshold value P3th (i.e., pressure value has crossed the threshold value from above to below), and the last value P3(n−1) detected at this last time is assumed to be a peak value Pm.

After the processing unit 120 receives a race start signal from a smartphone SP, the step signal generator 128 detects peaks of the pressure values $P3_R$, $P3_L$ varying according to the motions of an occupant P, and computes a peak value Pm. The detection of peaks and the computation of a peak value Pm may be executed in such a manner as executed by the calibration processor 127. The step signal generator 128 then computes a step intensity F ($F_R$, $F_L$) that is a leg-lift motion scale. The step intensity F may be indicated by the magnitude of the peak, i.e., a value obtained by subtraction of the peak value Pm from the normal pressure $P3_n$. In this embodiment, the obtained value is normalized by the normal pressure P3n so as to eliminate variations caused by largeness of the build of an occupant P. For example, the step intensity F may be given as follows:

$$F=(P3_n-Pm)/P3_n$$

The step signal generator 128 proceeds, upon detection of a peak of the pressure values P3R, P3L, to output the peak value Pm and the step intensity F to the smartphone SP. In this way, the step signal generator 128 outputs a signal based on the change in the pressure values P3 acquired from the pressure sensors PS3.

On the other hand, the game processing unit 210 of the smartphone SP executes, upon startup of an application (app), a game proceeding process. The game processing unit 210 comprises an entry reception processing section 211, a calibration instruction section 212, a character locomotion processing section 213, an imitative word determination section 214, and a result output section 219. The game processing unit 210 stores signals received from the control unit 100 together with times of receipt in the storage unit 290. The storage unit 290 is used, where deemed appropriate, to store data necessary for computation, processing, etc.

Moreover, the game processing unit 210 is configured to transmit data such as traveled distances L as computed, results of exercises, etc. to the control unit 100, where appropriate, to share the data with smartphones SP associated with other vehicle seats S. The control unit 100 accumulates these data in the storage unit 190.

Figure 30:
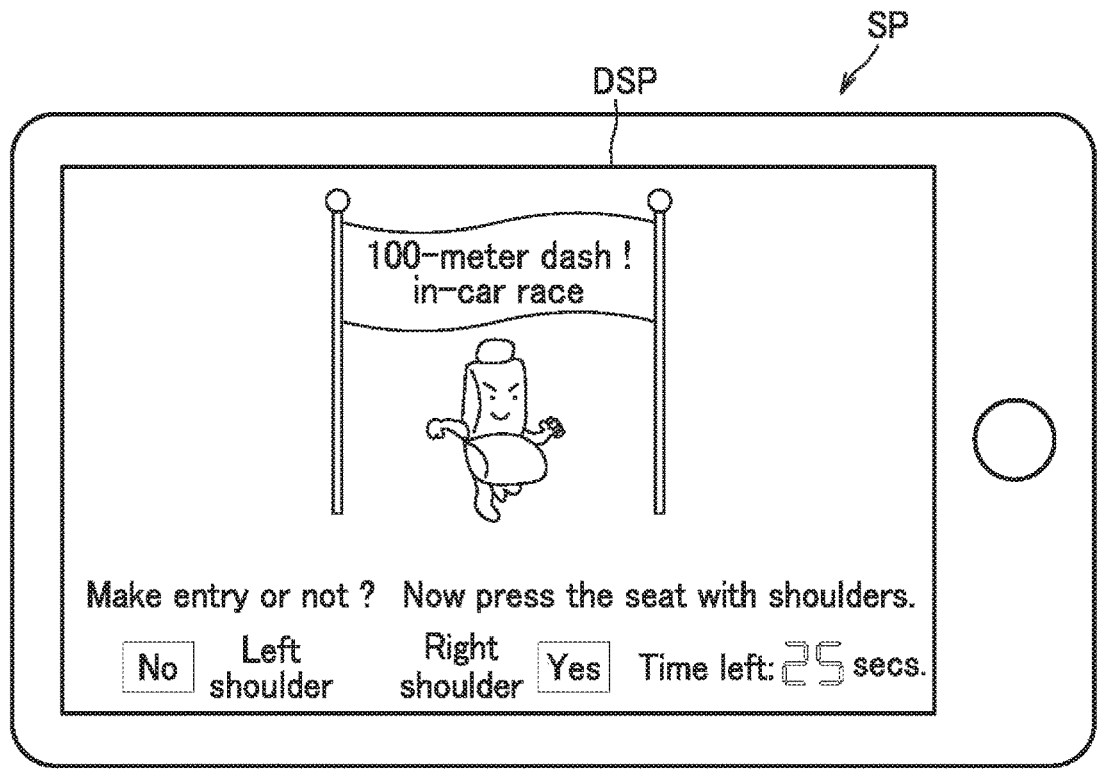
FIG. 30 is an example of a start screen.

The entry reception processing section 211 shows a start screen for reception of entry on the display DSP, transmits an entry reception signal to the control unit 100, and waits for an affirmative-reply signal or a negative-reply signal from the control unit 100 for a predetermined period of time. The start screen displays a notification for prompting the occupant P to do a motion, for example, as shown in FIG. 30, which includes texts such as "Make entry or not? Now press the seat with shoulders", and representations of "No, left shoulder, right shoulder, Yes". It is to be understood that the representations of Yes and No may each have a function as a button for furnishing the smartphone SP with the affirmative-reply signal or the negative-reply signal that can be generated with a touch of the display DSP. The entry reception processing section 211 proceeds, upon receipt of the affirmative-reply signal, to execute a game proceeding process, and proceeds, upon receipt of the negative-reply signal, to bring the app to an end without executing the game proceeding process. If the predetermined period of time has elapsed without receiving the affirmative-reply signal or the negative-reply signal, the game processing unit 210 then transmits a reception close signal to the control unit 100, and brings the app to an end.

The calibration instruction section 212 shows a calibration screen, and transmits a calibration start signal to the control unit 100, and receives signals related to calibration from the control unit 100 for a predetermined period of time. After a lapse of the predetermined period of time, the calibration instruction section 212 outputs a calibration end signal to the control unit 100.

The character locomotion processing section 213 operates during a 100-meter race, and upon receipt of a step intensity F causes a character on the display DSP to move toward the finish line. The amount of locomotion in this operation is determined in accordance with the magnitude of the step intensity F. The character locomotion processing section 213 may, for example, cause the character to move a distance F [m] toward the finish line.

The imitative word determination section 214 operates during a 100-meter race, and determines, and outputs on the display DSP, an imitative word that expresses a way how an occupant P is running (onomatopée or mimetic representation such as "Yochi-yochi (it looks as if toddling)"). Determination of the imitative word may be made, for example, based upon the step cycle TS that is a time interval at which the occupant P is moving his/her legs by comparison with the determination conditions shown in FIG. 22. The step cycle TS is the time interval of the step intensity F received from the control unit 100; however, as the time interval at which the step intensity F is received is not regular, an average time interval for the past 20 m can be adopted for computation.

In the present embodiment, for the purpose of reducing the effect of variations among individual occupants P, the determination of the imitative word expression is made by comparing a value given by division of the step cycle TS by the normal step cycle $TS_n$ with a threshold value. For example, $TS/TS_n$ not smaller than 1.5, which means that the cycle is long, is assigned to "fura-fura (tottering)"; $TS/TS_n$ not smaller than 1.2 and smaller than 1.5 to "nosshi-nosshi (lumping along)"; $TS/TS_n$ not smaller than 0.7 and smaller than 1.2 to "suta-suta (walking at brisk pace)"; $TS/TS_n$ smaller than 0.7 to "dota-dota (walking with heavy steps noisily)", etc.

The result output section 219 operates after an occupant P finishes in a 100-meter dash game, and determines, and outputs on the display DSP, the result of exercise and recommendations. In addition, the result of exercise is transmitted to the control unit 100.

To be more specific, the result output section 219 determines, as the result of exercise, an exercise level, a quantity of exercise, an exercise intensity, and a recommendation.

The exercise level is determined by performing a lookup in the exercise level determination table of FIG. 23 based on the number of steps taken during a 100-meter race. For example, the exercise level determination table lists predefined items such as "slow rambling" assigned to the number of steps not greater than 60, "usual daily-life walking" to the number of steps ranging from 61 to 110, "exercise walking" to the number of steps ranging from 111 to 140, "jogging" to the number of steps ranging from 141 to 240, and "dashing" to the number of steps not smaller than 240, etc.

The quantity of exercise may be found for example by computing a cumulative value of step intensities F measured during a 100-meter race.

The exercise intensity is represented by METs (metabolic equivalents). The value of the exercise intensity may be determined for example by multiplying the number of steps taken during a 100-meter race by a predetermined coefficient.

The recommendation may be determined by performing a lookup in the recommendation table stored beforehand in the storage unit 290. The recommendation table may be formulated for example with predetermined recommendations associated with parameters such as the numbers of steps, record times for a 100-meter race, average step cycles, etc. The recommendations can be determined by performing a lookup with these parameters obtained after finishing in the 100-meter race.

After making a determination of the exercise level, the quantity of exercise, the exercise intensity and the recommendation, the result output section 219 outputs these results on the display DSP.

Next, a description will be given of an example of processes of the control unit 100 and the app, as well as other processes of the game processing unit 210, with reference to the flowcharts.

To begin with, the process of the control unit 100 will be described below.

Processes of FIG. 24 to FIG. 27 are executed repeatedly.

Figure 24:
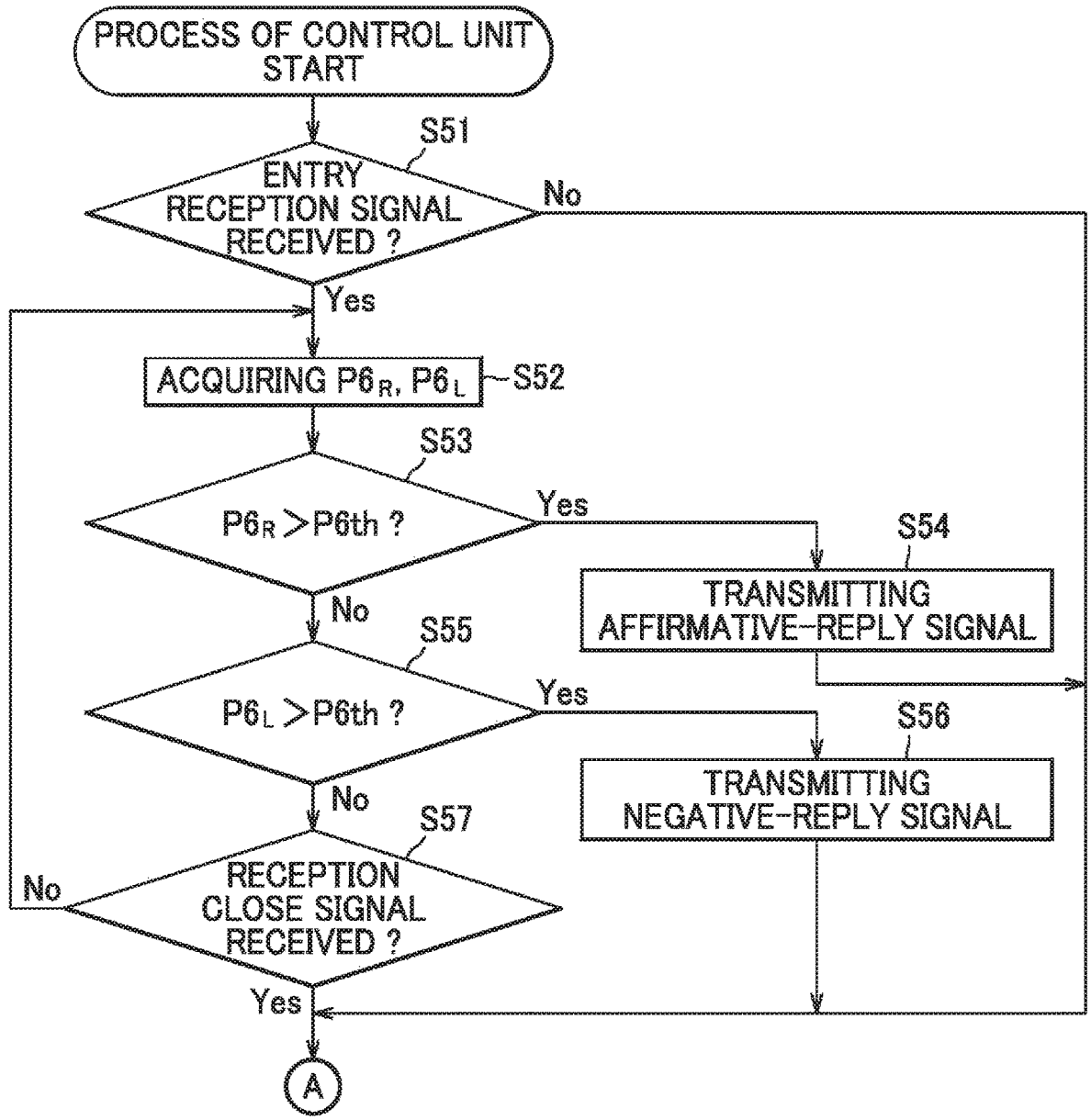
FIG. 24 is a flowchart of an example of the process of the control unit, showing a subset of steps for processing entry into a game.

As shown in FIG. 24, the processing unit 120, at the outset, executes steps S51 to S57 related to the entry into the game. To be more specific, first, a determination is made as to whether or not an entry reception signal has been received (S51).

If it is determined that an entry reception signal has been received (Yes, S51), the processing unit 120 then acquires pressure values $P6_R$, $P6_L$ (S52), and makes a determination as to whether or not the right pressure value $P6_R$ is greater than the threshold value $P6th$ (S53). If $P6_R$ is greater than $P6th$ (Yes, S53), then an affirmative-reply signal is transmitted (S54), and the process related to the entry into the game is brought to an end.

If $P6_R$ is not greater than $P6th$ (No, S53), the processing unit 120 then makes a determination as to whether or not the left pressure value $P6_L$ is greater than $P6th$ (S55). If $P6_L$ is greater than $P6th$ (Yes, S55), then a negative-reply signal is transmitted (S56), and the process related to the entry into the game is brought to an end.

If P6$_L$ is not greater than P6th (No, S55), the processing unit 120 then makes a determination as to whether or not a reception close signal has been received (S57), and if not received (No, S57), then the process starting from step S52 is repeated, while if received (Yes, S57), then the process related to the entry into the game is brought to an end.

Figure 25:
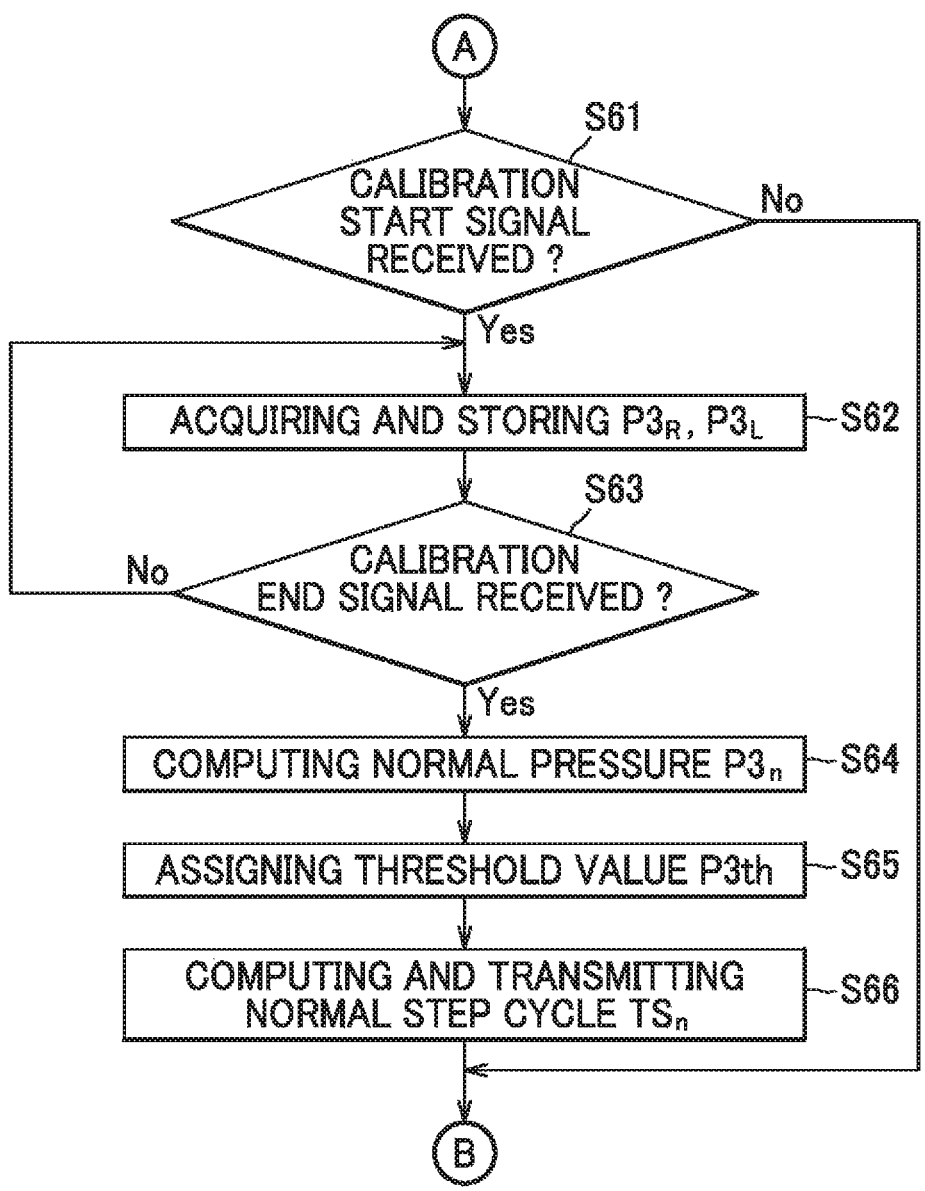
FIG. 25 is a flowchart of an example of the process of the control unit, showing a subset of steps for calibration.

After the process related to the entry into the game comes to an end, the calibration processor 127 of the processing unit 120 executes steps S61 to S66 related to the calibration process, as shown in FIG. 25.

The processing unit 120 makes a determination as to whether or not a calibration start signal has been received (S61), and if received (Yes, S61), then acquires and stores pressure values P3$_R$, P3$_L$ (S62). Subsequently, a determination is made as to whether or not a calibration end signal has been received (S63), and steps S62 to S63 are repeated until after receipt of that signal, i.e., as long as no such signal is received (No, S63), while once the signal is received (Yes, S63), then the process goes to step S64.

In step S64, the calibration processor 127 computes a normal pressure P3$_n$ based upon the pressure values P3$_R$, P3$_L$ acquired during a predetermined period of time and stored. Then, a threshold value P3th is set based upon the normal pressure P3$_n$ (S65). In addition, a normal step cycle TS$_n$ is computed, and transmitted to the smartphone SP (S66).

In step S61, if the calibration start signal has not been received (No), then the calibration processor 127 proceeds to step S70 (see FIG. 26) without executing the calibration process.

Next, the processing unit 120 executes a process of steps S70 to S80 related to a race.

Figure 26:
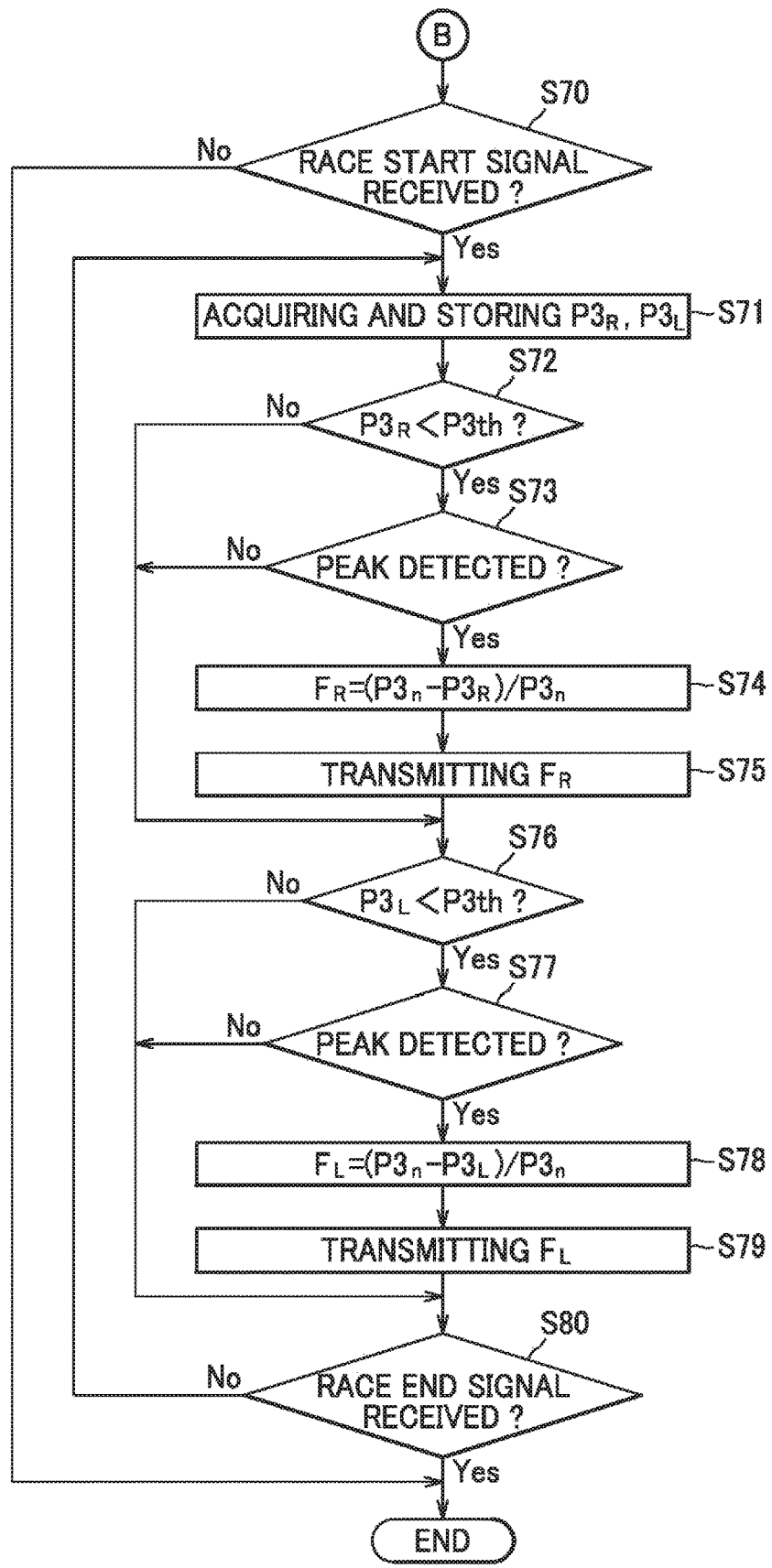
FIG. 26 is a flowchart of an example of the process of the control unit, showing a subset of steps for processing a race.

As shown in FIG. 26, first, the processing unit 120 makes a determination as to whether or not a race start signal has been received from the smartphone SP (S70). If the race start signal has not been received (No, S70), then the processing unit 120 brings the process to end. If the race start signal has been received (Yes, S70), then the step signal generator 128 acquires and stores the pressure values P3$_R$, P3$_L$ (S71).

Subsequently, a determination is made as to whether or not the right pressure value P3$_R$ is smaller than the threshold value P3th (S72), and if smaller (Yes, S72), then a determination is made as to whether or not a peak has been detected from the last value and the present value of the pressure values P3$_R$ (S73). If a peak has been detected (Yes, S73), then the step signal generator 128 computes a step intensity F$_R$ from the normal pressure P3$_n$ and the pressure value P3$_R$ (S74). The step intensity F$_R$ thus computed is transmitted to the smartphone SP (S75).

On the other hand, if the right pressure value P3$_R$ is not smaller than the threshold value P3th (No, S72), or no peak has been detected (No, S73), then the step signal generator 128 proceeds to step S76 without computing and transmitting the step intensity F$_R$.

In steps S76 to S79, the step signal generator 128 executes the processes of detecting a peak, and computing and transmitting a step intensity F$_L$ for the left pressure values P3$_L$. As these processes are similar to those of steps S71 to S75, a description thereof will be omitted.

In step S80, the processing unit 120 makes a determination as to whether or not a race end signal has been received, and if not received (No, S80), then the process starting from step S71 is repeated, while if received (Yes, S80), then the process is brought to an end.

Next, a description of a process of the app (game processing unit 210) of the smartphone SP will be given below.

Figure 27:
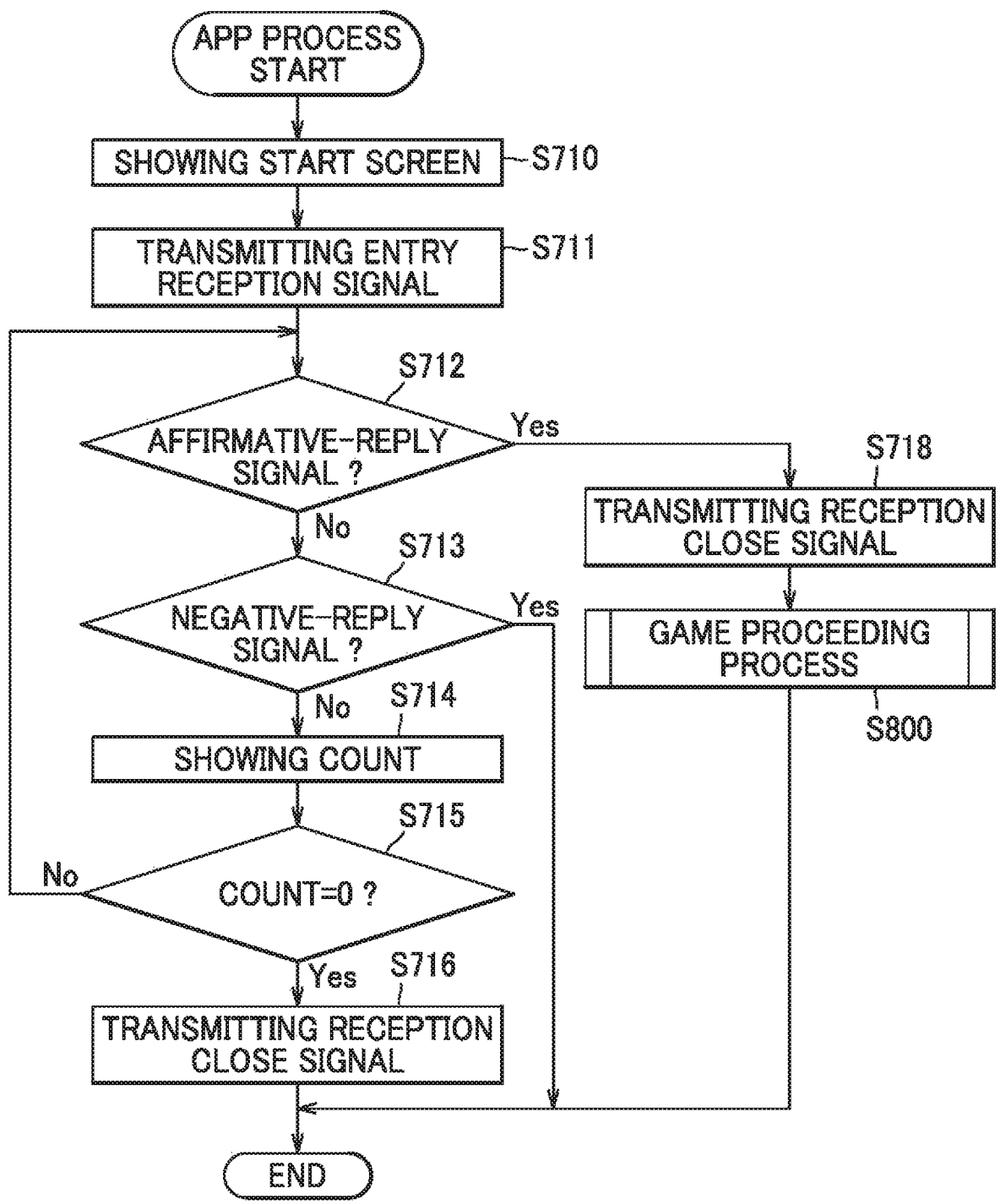
FIG. 27 is a flowchart of an example of the process of an app.

When an app (application) is activated, the smartphone SP starts the process of the app, and shows a start screen on the display DSP (S710) as shown in FIG. 27. The start screen is, for example, a screen as shown in FIG. 30. In the start screen, the text "Make entry or not? Now press the seat with shoulders" and an instruction showing that the left shoulder action signals for negative reply (equivalent to saying 'No') and the right shoulder action signals for affirmative reply (equivalent to saying 'Yes') are displayed. In addition, the remaining time to make a reply for obtaining entry is shown.

The entry reception processing section 211 transmits an entry reception signal to the control unit 100 (S711). The entry reception processing section 211 makes a determination as to whether or not an affirmative-reply signal has been received (S712), and if received, (Yes, S712), then transmits a reception close signal to the control unit 100 (S718), proceeding to execute a game proceeding process (S800), and eventually brings the process to an end. The game proceeding process will be described later.

If the affirmative-reply signal has not been received (No, S712), then the entry reception processing section 211 makes a determination as to whether or not a negative-reply signal has been received (S713), and if received (Yes, S713), then brings the process to an end.

On the other hand, if the negative-reply signal has not been received (No, S713), then the entry reception processing section 211 shows a count indicative of the remaining time (S714) and makes a determination as to whether or not the count has reached zero (S715). If the count has not reached zero (No, S715), then the process of entry reception as proceeding from step S712 is continued, while if the count has reached zero (Yes, S715), then a reception close signal is transmitted to the control unit 100 (S716), and the process is brought to an end.

Figure 28:
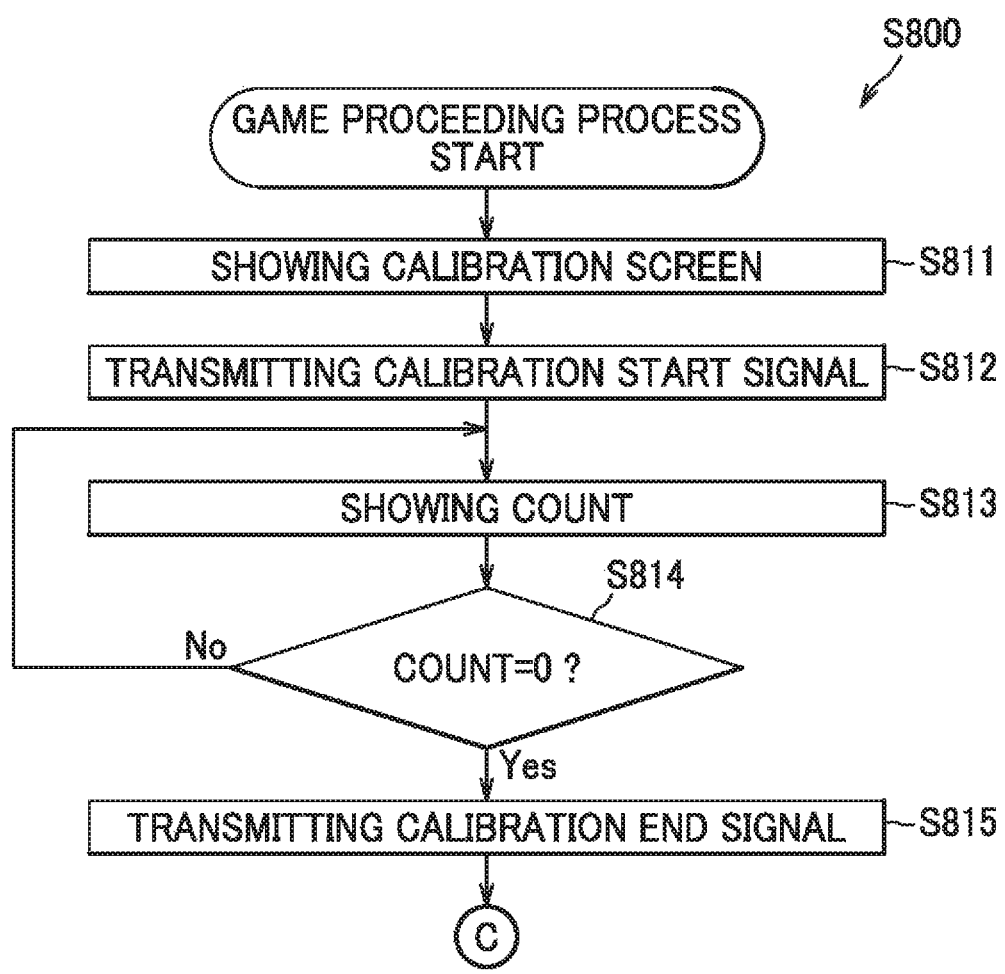
FIG. 28 shows a subset of steps for calibration in a game proceeding process.
Figure 31:
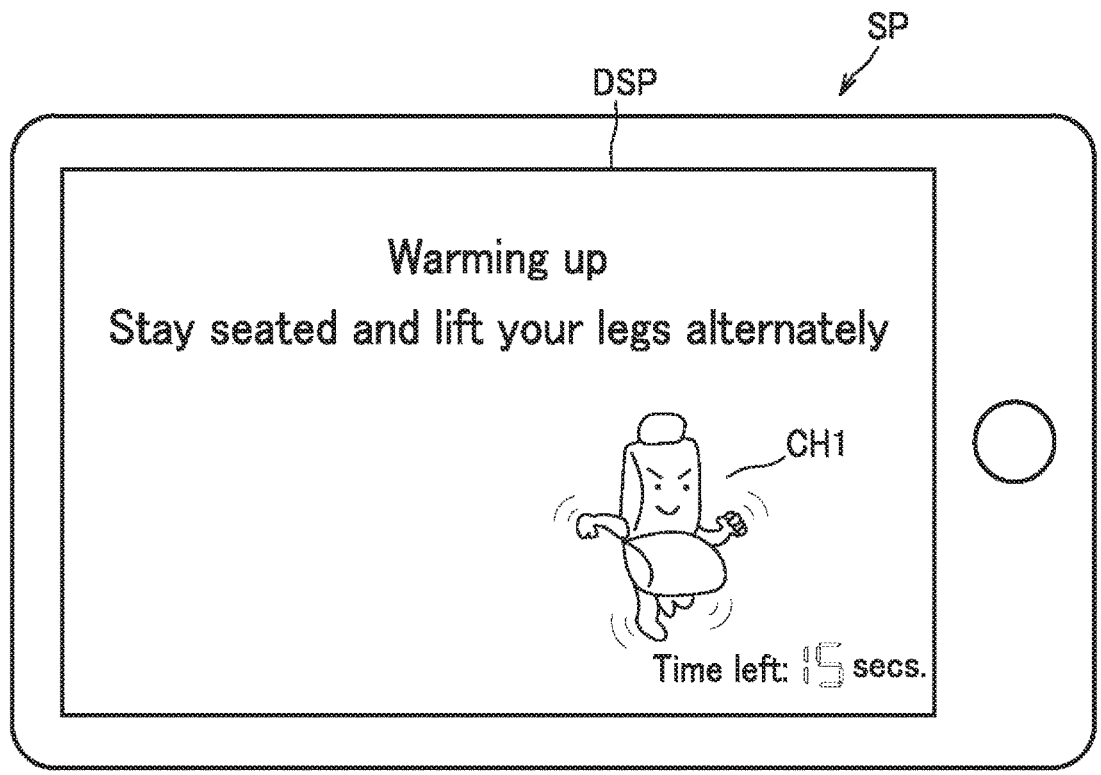
FIG. 31 is an example of a warm-up screen.

As shown in FIG. 28, in the game proceeding process (S800), first, the calibration instruction section 212 shows a calibration screen on the display DSP (S811). The calibration screen displays, for example, as shown in FIG. 31, an instruction in text format "Warming up, stay seated and lift your legs alternately" and the remaining time for calibration. An animated cartoon of a running character CH1, such as a personified seat may be shown on the display DSP to help an occupant P to easily understand what to do.

Subsequently, the calibration instruction section 212 transmits a calibration start signal to the control unit 100 (S812). Then, the updated count of the remaining time is shown on the display DSP (S813), and a determination is made as to whether the count has reached zero (S814). If the count has not reached zero (No, S814), then the showing of the decrementing count in step S813 continues; if the count has reached zero (Yes, S814), then the calibration end signal is transmitted to the control unit 100 (S815).

Figure 29:
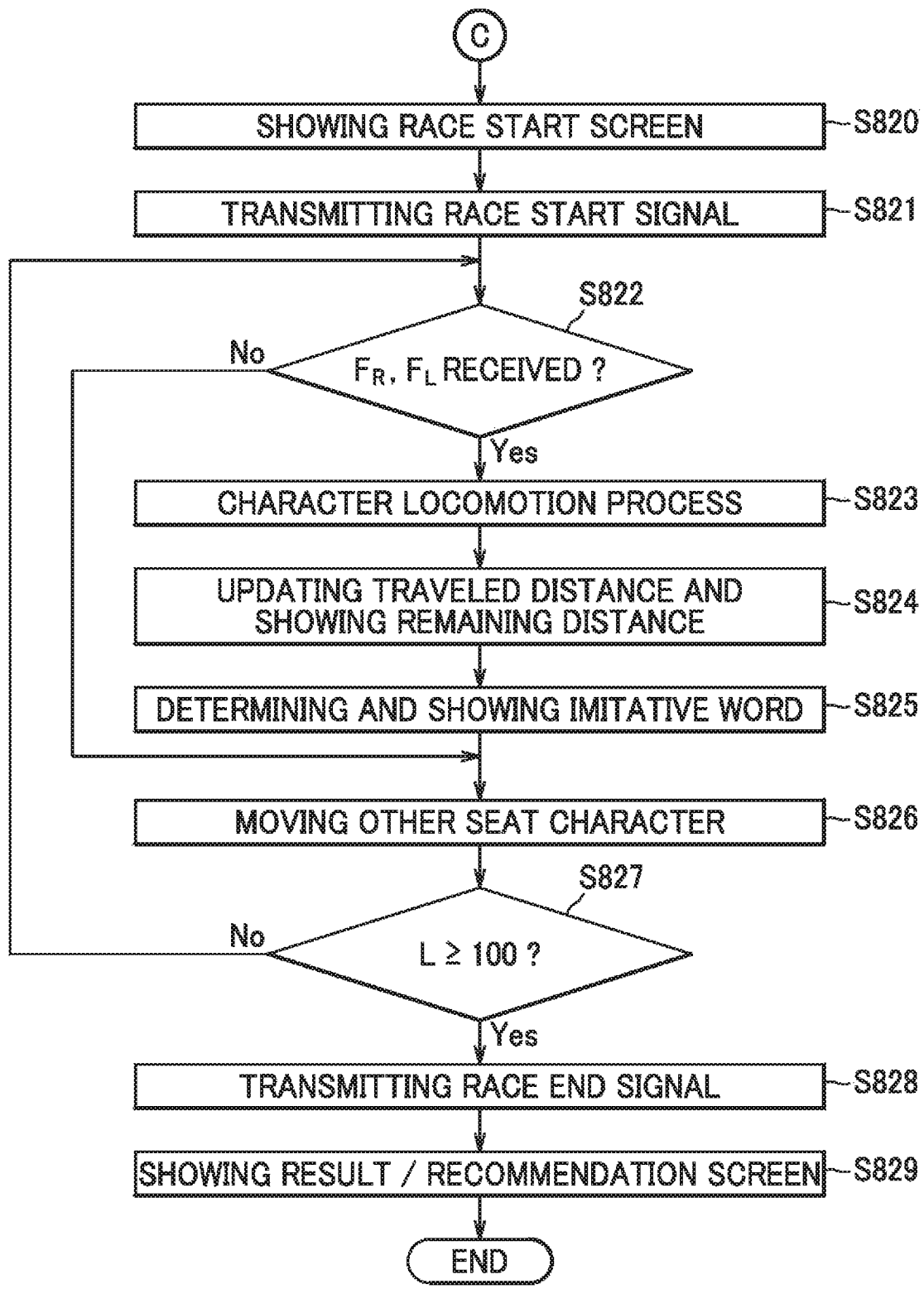
FIG. 29 is a subset of steps for processing a race in the game proceeding process.
Figure 32:
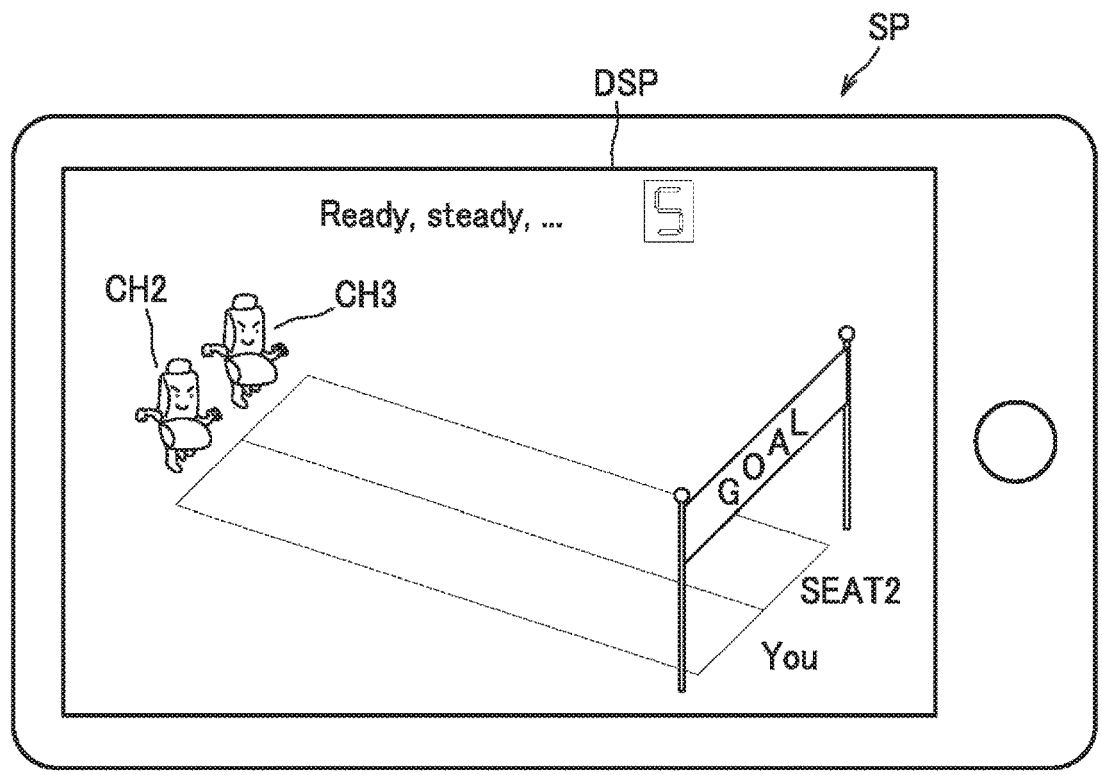
FIG. 32 is an example of a start screen for a 100-meter dash game.

If the calibration comes to an end, the game processing unit 210 then shows a race start screen as shown in FIG. 29 (S820). The race start screen displays, for example, as shown in FIG. 32, a text message "Ready, steady . . . " and a numeric character indicative of a countdown for the start. In the race screen, the 100-meter race tracks, and seat-personified characters CH2, CH3 on the respective tracks are also displayed.

For example, if a plurality of tracks are shown and there is an entry of another occupant P competing in the same race, then text labels indicating players, i.e., "You" and "SEAT 2" of which the latter is a label of an entrant seated on another seat, are shown on the respective tracks.

With the race start screen being shown on display, when the race starts after completion of the countdown (relevant steps omitted from the flowchart), the game processing unit 210 transmits a race start signal to the control unit 100 (S821). Subsequently, the character locomotion processing section 213 makes a determination as to whether or not the step intensities $F_R$, $F_L$ have been received (S822). If received (Yes, S822), then the character locomotion processing section 213 executes a process of moving a character CH2 according to the magnitudes of the step intensities $F_R$, $F_L$ (S823). The traveled distances L are updated, and the traveled distances L are transmitted to the control unit 100. Further, the character locomotion processing section 213 shows a remaining distance on the display DSP (S824).

Figure 33:
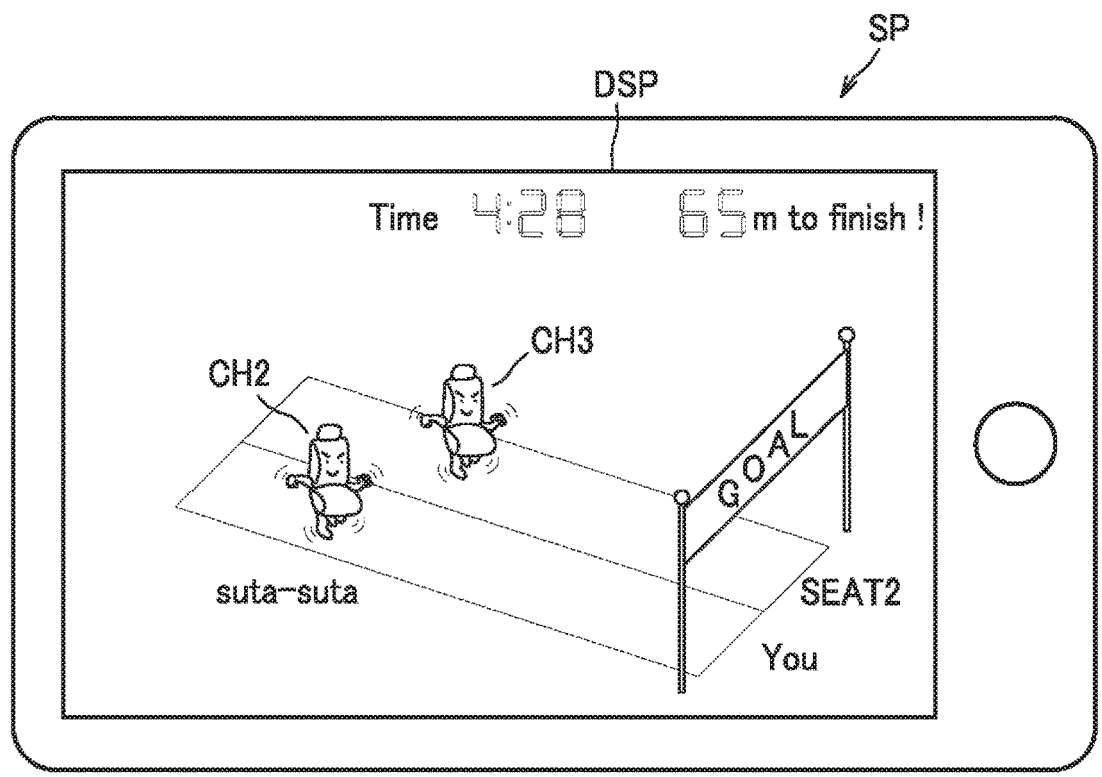
FIG. 33 is an example of a screen shown during the 100-meter dash game.

Next, the imitative word determination section 214 determines an imitative word to be shown, from the step cycle TS and the normal step cycle $TS_n$, and shows the same on the display DSP (S825). Accordingly, during the race, an animated cartoon of characters CH2, CH3 running on the respective tracks, the remaining distance, and an imitative word such as "suta-suta (walking at brisk pace)" are displayed, as shown in FIG. 33. Moreover, the game processing unit 210 shows a time lapsed after the start.

If the step intensities $F_R$, $F_L$ have not been received (No, S822), then the character locomotion processing section 213 proceeds to step S826 without executing steps S823 to S825.

Subsequently, the game processing unit 210 acquires a traveled distance L of the character CH3 for the other seat occupant P, and moves the other seat character CH3, on an as-needed basis (S826).

Figure 34:
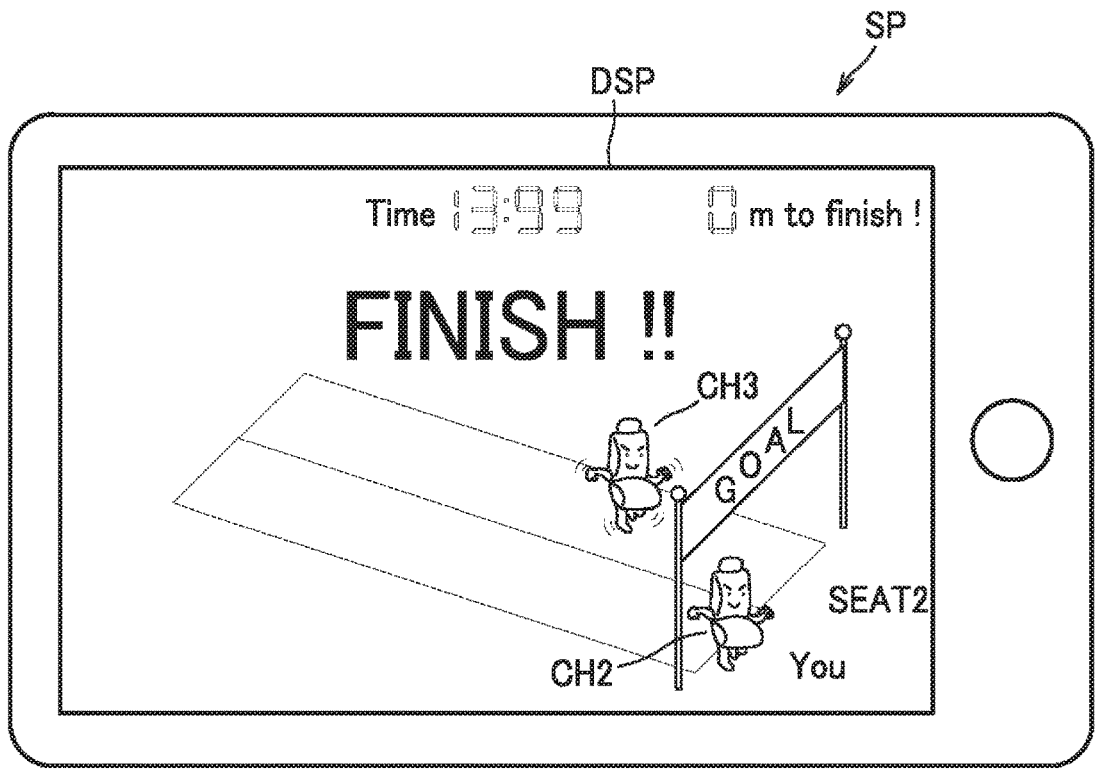
FIG. 34 is an example of a screen shown at the time of finishing in the 100-meter dash game.

Next, the character locomotion processing section 213 makes a determination as to whether or not the traveled distance L is equal to or greater than 100 (S827), and if not equal to or greater than 100 (No, S827), then repeats the process of the race starting from step S822. On the other hand, if the traveled distance L becomes equal to or greater than 100 (Yes, S827), then a race end signal is transmitted to the control unit 100 (S828). At the end of the race, a screen for example as shown in FIG. 34 is displayed. In this screen, the remaining distance is shown to be zero meter, and a time recorded at the finish of the race is indicated.

Figure 35:
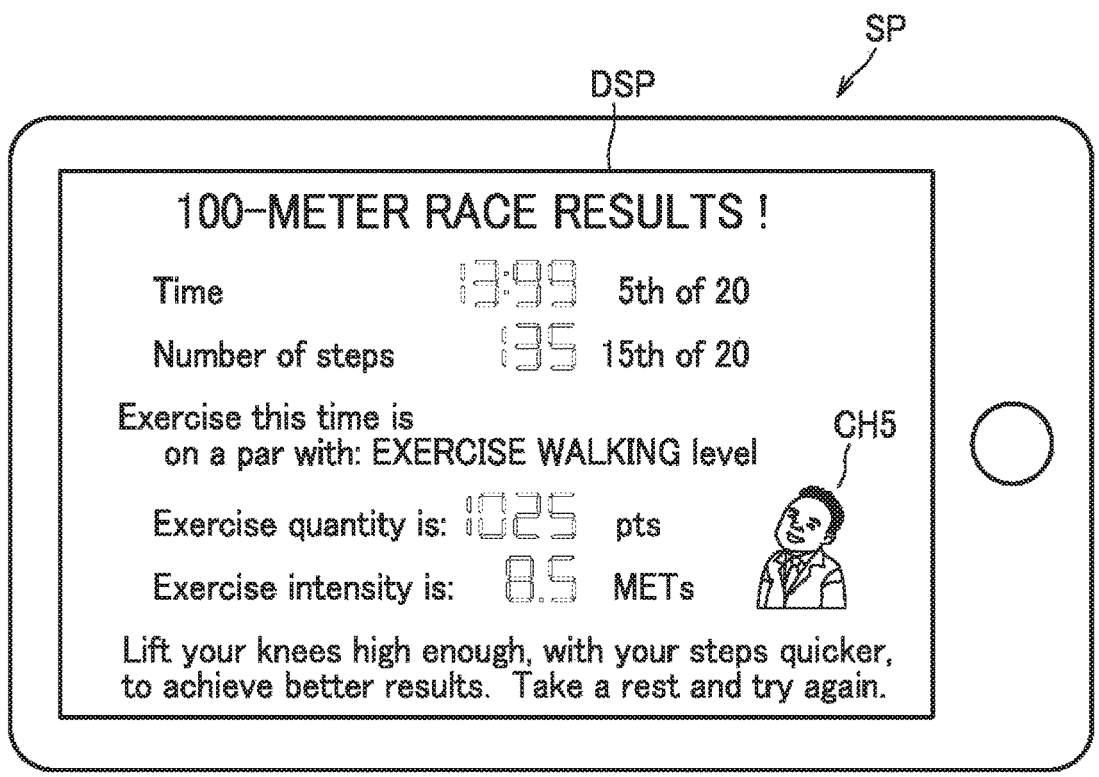
FIG. 35 is an example of a result screen of the 100-meter dash game.

Then, the result output section 219 determines, as a result of the exercise, an exercise level, a quantity of exercise, an exercise intensity, and a recommendation, and shows them on the display DSP (S829). The result screen is, for example, a screen as shown in FIG. 35. In the result screen, the ranking determined among all the past players as from data accumulated up to then in the control unit 100 may be shown. Further, if the result is good, a character CH5 with pleased facial expressions may be shown, while if the result is not good, a character with regrettable facial expressions may be shown.

After the result output section 219 displays the result of exercise, the process of app comes to an end.

As has been described above, with the vehicle seat S according to the present embodiment, the following advantageous effects can be achieved.

Since the controller 100 outputs, to the smart phone SP, the pressure values acquired from the pressure sensors PS1 to PS6 as signals for operating the game app of the smartphone SP, the occupant P seated on the vehicle seat S can operate the smartphone SP by moving his/her legs and/or shoulders, on the seat body S0.

Therefore, the operation of the smartphone SP which would conventionally be performed by hand can be carried out through motions of his/her body on the seat body S0.

Accordingly, one who becomes tired in a vehicle can move his/her body in moderation to feel refreshed.

Since the pressure sensors PS1 to PS6 are capable of detecting the states of the seat surfaces SF1, SF2 that face a seated occupant P, the occupant P can easily access the pressure sensors PS1 to PS6. In other words, the occupant can operate the on-board device by changing the states of the seat surfaces, and thus can operate the smartphone SP with increased ease.

Since the affirmative-reply signal and the negative-reply signal are generated on condition that the pressure values P6 exceed the threshold value P6*th*, and the step intensity F as well is outputted on condition that the pressure value P3 has crossed the threshold value P3*th* from above to below, an inadvertent operation of the smartphone SP that is counter to the intent of the occupant P can be restrained.

Since the affirmative-reply signal is generated based on the measurement value of the right pressure sensor PS6, and the negative-reply signal is generated based on the measurement value of the left pressure sensor PS6, an operation error can be restrained.

Although the second embodiment has been described above, the present invention is not limited to the above-described embodiment. Specific configurations may be modified where appropriate without departing from the gist of the present invention.

For example, in the above-described embodiment, the operation of the 100-meter dash game as an example of a game is illustrated, but the same applies to the operation of other games. Moreover, the on-board device which is to be operated may not be limited to the smartphone, but may be a PC, a navigation system or the like. Furthermore, the device is not limited to one having a display as those enumerated above, but may be a telephone, an audio system, or the like. It is to be understood that the on-board device in the present embodiment is not intended to encompass a vehicle itself (i.e., the driving operation of a vehicle is not a target). However, as long as the operation is not directed to driving of a vehicle, the on-board device may be provided as stationary equipment fixed to a vehicle, and the operation may be any one to be performed on an air conditioner, or to actuate a window pane to move up and down.

Since the operation of the on-board device is rendered achievable by a body motion on a vehicle seat as described above, any person unwilling to use a hand, or even a person physically challenged and thus unable to use a hand, can operate an on-board device by moving part of his/her body, or tensing his/her muscle or otherwise.

In the above-described embodiment, the sensors are exemplified by the pressure sensors, but the sensors may be any other kind of sensors, such as capacitance sensors, etc. In cases where the pressure is to be measured, pressure distribution sensors may be used instead.

In the above-described embodiment, the control unit 100 and part of the smartphone SP together form a controller, but the control unit only may constitute a controller, or the smartphone only may constitute a controller. A computer with communications capabilities, such as a cloud computer, may be provided in another location, and such a cloud computer may constitute a controller in part or in entirety.

The signals for use in operation of an on-board device as defined in the present embodiment may be comprised of electric power in itself for driving a motor, etc.

In the above-described embodiment, the controller and the smartphone are connected by radio communication, but may be connected by wire communication.

In the above-described embodiment, the motion for operating an on-board device is exemplified by leg up-down motion and shoulder press-against-seat-back motion only, but an alternative configuration may be such that an on-board device is operated by other motions such as an upper-body twisting, rocking (to-and-fro or left-and-right) or turning motion, or buttocks rocking motion, etc.

The vehicle seat according to the second embodiment may be a seat for a vehicle other than an automobile, such as a railcar, or a seat for a vehicle other than a car, such as a ship or aircraft.

Any of the elements explained in relation to the exemplified embodiments and illustrative modified examples disclosed in this description may be implemented in combination as desired.

The invention claimed is:

1. A seat comprising:
a seat body;
sensors configured to acquire measurement values for use in identifying motion of an occupant seated on the seat body, the measurement values including values of pressure from the occupant seated on the seat body; and
a controller connected to the sensors and thereby allowed to acquire the measurement values from the sensors,
wherein the seat body comprises a seat cushion and a seat back,
wherein the sensors comprise:
a first cushion sensor provided at the seat cushion in a position thereof corresponding to buttocks of the occupant,
a second cushion sensor provided at the seat cushion and located farther frontward than the first cushion sensor,
a first back sensor provided at the seat back and located in a lower position thereof, and
a second back sensor provided at the seat back and located above the first back sensor,
wherein the controller is configured to:
identify the motion of the occupant based on a combination of changes of outputs of at least two sensors selected from a group consisting of the first cushion sensor, the second cushion sensor, the first back sensor, or the second back sensor, the controller comprising:
a motion instruction unit configured to give the occupant an instruction to perform a predetermined motion; and
a motion determination unit configured to:
identify the motion of the occupant based on changes of outputs of the at least two sensors compared to measurement values of the at least two sensors acquired when the occupant is in a reference posture,
determine, after the motion instruction unit gives the instruction, whether or not the occupant is performing the predetermined motion,
wherein the changes of outputs of the at least two sensors are determined by comparing the outputs of the at least two sensors with stored threshold values, and
wherein the threshold values are set for each occupant, and
wherein the motion that the controller is configured to identify includes a motion of the occupant lifting a heel or foot up from a floor.

2. The seat according to claim 1, wherein the controller is configured to:
determine that a heel lift motion has been performed if a pressure value of the first cushion sensor increases to be greater than a pressure value of the first cushion sensor acquired when the occupant is in the reference posture and if a pressure value of the second cushion sensor decreases to be less than a pressure value of the second cushion sensor acquired when the occupant is in the reference posture.

3. The seat according to claim 1, wherein the controller is configured to:
determine that a foot lift motion has been performed if pressure values of the first cushion sensor and the first back sensor increase to become greater than the pressure values of the first cushion sensor and the first back sensor acquired when the occupant is in the reference posture and if a pressure value of the second cushion sensor decreases to become less than a pressure value of the second cushion sensor acquired when the occupant is in the reference posture.

4. The seat according to claim 1, wherein the controller is configured to:
determine that a sit-up-straight motion has been performed if a pressure value of the first cushion sensor increases to become greater than a pressure value of the first cushion sensor acquired when the occupant is in the reference posture and if a pressure value of the first back sensor decreases to become less than a pressure value of the first back sensor acquired when the occupant is in the reference posture.

5. The seat according to claim 1, wherein the controller is configured to:
determine that a scapulae press-against-seat-back motion has been performed if pressure values of the first cushion sensor and the second back sensor increase to become larger than pressure values of the first cushion sensor and the second back sensor acquired when the occupant is in the reference posture and if a pressure value of the first back sensor decreases to become less than a pressure value of the first back sensor acquired when the occupant is in the reference posture.

6. The seat according to claim 1,
wherein the first back sensor comprises at least one right first back sensor and at least one left first back sensor,
wherein the first cushion sensor comprises at least one right first cushion sensor and at least one left first cushion sensor,
wherein the second back sensor comprises at least one right second back sensor and at least one left second back sensor, and
wherein the controller is configured to:
determine that an upper-body-right-turn motion has been performed if pressure values of the right first cushion sensor and the right first back sensor increase to become larger than pressure values of the right first cushion sensor and the right first back sensor acquired when the occupant is in the reference posture and if pressure values of the left first back sensor and the left second back sensor decrease to become less than pressure values of the left first back sensor and the left second back sensor acquired when the occupant is in the reference posture, and
determine that an upper-body-left-turn motion has been performed if pressure values of the left first cushion sensor and the left first back sensor increase to become larger than pressure values of the left first cushion sensor and the left first back sensor acquired when the occupant is in the reference posture and if pressure values of the right first back sensor and the right second back sensor decrease to become smaller than pressure values of the right first back sensor and the right second back sensor acquired when the occupant is in the reference postures.

7. The seat according to claim 1, wherein the second back sensor is located above a position distanced 300 mm upward from a seat surface of the seat cushion as measured along a seat surface of the seat back.

8. The seat according to claim 1, wherein the second cushion sensor is located frontward of a position distanced 280 mm frontward from a seat surface of the seat back as measured along a seat surface of the seat cushion.

9. The seat according to claim 1, wherein the motion instruction unit is configured to give the occupant an instruction to perform the predetermined motion by at least one signal from a group consisting of sound, light, image, moving image, textual characters, vibrations, warmth sensation, and coldness sensation.

10. The seat according to claim 1, wherein if the motion determination unit determines that the occupant is not performing the predetermined motion, the motion instruction unit then gives the instruction again to perform the predetermined motion.

11. The seat according to claim 1, wherein if the motion determination unit determines that the predetermined motion the occupant is performing is deficient in scale, the motion instruction unit then gives the occupant an instruction to perform the predetermined motion on a larger scale.

12. The seat according to claim 1, wherein if the motion determination unit determines that a motion the occupant is performing is different from the motion instructed by the motion instruction unit, the motion instruction unit then notifies the occupant of a proper way to perform the motion.

13. The seat according to claim 1, wherein the controller is:
connected to and thus allowed to communicate with an on-board device, which is to be operated, the on-board device being located in a vehicle in which the seat body is installed; and
configured to output, based on the measurement values, a signal for operating the on-board device.

14. The seat according to claim 13, wherein the sensors are so located as to be allowed to detect a state of a seat surface that faces an occupant seated on the seat body.

15. The seat according to claim 13, wherein the on-board device includes a display, and
wherein the controller is capable of outputting a signal for manipulating a cursor or an icon shown on the display.

16. The seat according to claim 13, wherein the controller is configured to output the signal based on the measurement values, provided that the measurement values exceed predetermined threshold values.

17. The seat according to claim 13, wherein the controller has operation modes that comprise a first operation mode in which the signal is outputted based on the measurement values, and a second operation mode in which the signal is not outputted, the controller is further configured to operate in the first operation mode only after providing notification to prompt the occupant to do a motion via the on-board device or other devices.

18. The seat according to claim 13,
wherein the sensors comprise a first pressure sensor and a second pressure sensor located in a position different from a position of the first pressure sensor, and
wherein the controller is further configured such that to an operation of the on-board device as determined based on a measurement value acquired from the first pressure sensor is assigned a first operation, and to an operation of the on-board device as determined based on a measurement value acquired from the second pressure sensor is assigned a second operation.

19. The seat according to claim 13, wherein the controller is configured to output the signal based on change of the measurement values acquired from the sensors.

20. The seat according to claim 13, wherein a plurality of seat bodies are provided in the vehicle, and the sensors are provided in each of the seat bodies,
wherein the controller is further configured to acquire the measurement values from each of the seat bodies, and to output the signal based on the measurement values.

21. The seat according to claim 1, wherein the first back sensor comprises a pair of lower sensors arranged side by side at the seat back, and a pair of middle sensors arranged side by side at the seat back in a position higher than a position of the pair of lower sensors,
wherein the second back sensor comprises a pair of upper sensors arranged side by side at the seat back in a position higher than the position of the pair of middle sensors of the first back sensor, and
wherein a distance between the position of the pair of upper sensors and the position of the pair of middle sensors is greater than a distance between the position of the pair of lower sensors and the position of the pair of middle sensors.

22. The seat according to claim 1, wherein the first cushion sensor comprises a pair of rear sensors arranged side by side at the seat cushion, and a pair of middle sensors arranged side by side at the seat cushion in a position frontward of a position of the pair of rear sensors,
wherein the second cushion sensor comprises a pair of front sensors arranged side by side at the seat cushion in a position frontward of the position of the pair of middle sensors of the first cushion sensor, and
wherein a distance between the position of the pair of front sensors and the position of the pair of middle sensors is greater than a distance between the position of the pair of rear sensors and the position of the pair of middle sensors.

* * * * *